(12) United States Patent
van Dongen et al.

(10) Patent No.: US 9,487,830 B2
(45) Date of Patent: Nov. 8, 2016

(54) DETERMINING THE REPLICATIVE HISTORY OF LYMPHOCYTES

(75) Inventors: Jacobus J. M. van Dongen, Nieuwerkerk aan den IJssel (NL); Thomasz Szczepanski, Zabrze (PL)

(73) Assignee: Erasmus Universiteit Rotterdam, Rotterdam (NL)

( * ) Notice: Subject to any disclaimer, the term of this patent is extended or adjusted under 35 U.S.C. 154(b) by 306 days.

(21) Appl. No.: 11/409,718

(22) Filed: Apr. 24, 2006

(65) Prior Publication Data

US 2007/0003951 A1    Jan. 4, 2007

Related U.S. Application Data

(63) Continuation-in-part of application No. PCT/NL2005/000761, filed on Oct. 24, 2005.

(60) Provisional application No. 60/622,317, filed on Oct. 25, 2004.

(51) Int. Cl.
  *C12Q 1/68* (2006.01)
  *C07H 21/04* (2006.01)

(52) U.S. Cl.
  CPC .......... *C12Q 1/6883* (2013.01); *C12Q 1/6876* (2013.01); *C12Q 1/6881* (2013.01); *C12Q 2600/156* (2013.01)

(58) Field of Classification Search
  None
  See application file for complete search history.

(56) References Cited

FOREIGN PATENT DOCUMENTS

| EP | 1849877 | | 10/2007 |
|---|---|---|---|
| WO | WO 2004/033728 | * | 4/2004 |
| WO | WO 2004/033728 A2 | | 4/2004 |
| WO | WO 2006/046860 A1 | | 5/2006 |
| WO | WO 2007/123392 A1 | | 11/2007 |

OTHER PUBLICATIONS

Zhu, Chengming et al. Ku86-deficient mice exhibit severe combined immunodeficienty and defecting processing of V(D)J recombination intermediates. 1996. Cell. vol. 86, 379-389.*

Hazenburg, Mette et al. T cell receptor excision circles as markers for recent thymic emigrants: basic aspects, technical approach, and guidelines for interpretation. 2001 Journal of Moelcular Medicine. vol. 79 pp. 631-640.*

Zhang, Linqi et al. Measuring recent thymic emigrants in blood of normal and HIV-1 infected individuals before and after effective therapy. 1999. Journal of Experimental Medicine. vol. 190 pp. 725-732.*

(Continued)

*Primary Examiner* — Amanda Haney
(74) *Attorney, Agent, or Firm* — Knobbe, Martens, Olson & Bear, LLP

(57) ABSTRACT

The invention relates to the field of immunology and immunodiagnostics. Provided is a method for determining the replicative history of a lymphocyte, preferably a B cell, the method comprising detecting a signal joint nucleotide sequence on an extrachromosomal circular excision product in the lymphocyte, wherein the excision product is deleted from a chromosome to give a chromosomal-coding joint nucleotide sequence, wherein the coding joint is retained in the chromosome, and detecting the coding joint nucleotide sequence in the lymphocyte. Also provided are primers, probes and a control cell for use in a method of the invention. A method provided herein is among others advantageously used to assess recovery of the precursor B-cell compartment, for example, in a patient following bone marrow transplantation

15 Claims, 12 Drawing Sheets

(56) References Cited

OTHER PUBLICATIONS van Dongen, JJM et al. Desgin and standardization of PCR primers and protocols for detection of clonal immunoglobulin and T cell receptor gene recombinations in suspect lymphoproliferations: report of the BIOMED-2 concerted action BMH4-CT98-3936. 2003 Leukemia. vol. 17 pp. 2257-2317.*

Walker, Nigel. Real Time and Quantitative PCR: Applications to Mechanism Based Toxicology. J Biochem Molecular Toxicology 2001 vol. 15 No. 3 pp. 121-127.*

GenBank Accession X05186 GI 33243 Aug. 4, 1992.*

Langerak et al. The Journal of Immunology Sep. 15, 2004 vol. 173 pp. 3878-3888.*

Jasper (The Journal of Immunology Dec. 15, 2003 vol. 171 pp. 6372-6380).* van der Velden (Leukemia 2002 vol. 16 pp. 928-936).*

Szczepanski (The Lancet Oncology 2001 vol. 2 pp. 409-417).*

Broers et al., Interleukin-7 improves T-cell recovery after experimental T-cell-depleted bone marrow transplantation in T-cell-deficient mice by strong expansion of recent thymic emigrants. Blood, Aug. 15, 2003, pp. 1534-1540, vol. 102, No. 4.

Geenen et al., Quantification of T cell receptor rearrangement excision circles to estimate thymic function: an important new tool for endocrine-immune physiology, Journal of Endocrinology, 2003, pp. 305-311, vol. 176.

Jasper et al., B Lymphocyte Development in Rabbit: Progenitor B Cells and Waning of B Lymphopoiesis, The Journal of Immunology, 2003, pp. 6372-6380, vol. 171.

Krenger et al., On the Relevance or TCR Rearrangement Circles as Molecular Markers for Thymic Output during Experimental Graft-versus-Host Disease, The Journal of Immunology, 2004, pp. 7359-7367, vol. 172.

Langerak et al., Unraveling the Consecutive Recombination Events in the Human IGK Locus, The Journal of Immunology, 2004, pp. 3878-3888, vol. 173.

PCT International Search Report, PCT/NL03/00690, dated Jun. 16, 2004.

Breit et al., "Human T Cell Leukemias with Continuous V(D)J Recombinase Activity for TCR-δ Gene Deletion", J Immunol. Nov. 1, 1997;159(9):4341-9.

Cook et al., "The human immunoglobulin $V_H$ repertoire", Immunology Today, vol. 16, No. 5, 1995, pp. 237-242.

Corbett et al., "Sequence of the human immunoglobulin diversity (D) segment locus: a systematic analysis provides no evidence for the use of DIR segments, inverted D segments, "minor" D segments or D-D recombination", J. Mol. Biol. (1997) 270, 587-597.

Folch et al., "The Human T Cell Recepto Beta Diversity (TRBD) and Beta Joining (TRBJ) Genes", Exp. Clin Immunogenet 2000; 17:107-114.

Gellrich et al., "Analysis of $V_H$-D-$J_H$ Gene Transcripts in B Cells Infiltrating the Salivary Glands and Lymph Node Tissues of Patients with Sjogren's Syndrome", Arthritis and Rheumatism, vol. 42, No. 2, Feb. 1999, pp. 240-247.

Janeway et al., "Immunobiology", $2^{nd}$ Edition, Current Biology Ltd., 1996, pp. 5:5-5:7 and 6:9-6:15.

LeFranc, Marie-Paule, "IMGT, the international ImMunoGeneTics database: a high-quality information system for comparative immunogenetics and immunology", Developmental and Comparative Immunology 26 (2002) 697-705.

LeFranc, Marie-Paule, "Nomenclature of the Human Immunoglobulin Heavy (IGH) Genes", Exp. Clin Immunogenet 2001; 18:100-116.

Ravetch et al., "Structure of the human immunoglobulin μ locus: Characterization of embryonic and rearranged J and D genes" , Cell, vol. 27, 583-591, Dec. 1981.

Ruiz et al., "The Human Immunoglobulin Heavy Diversity (IGHD) and Joining (IGHJ) Segments" Exp Clin Immunogenet 1999;16:173-184.

Scaviner et al., The Human T Cell Receptor Alpha Variable (TRAV) Genes, Exp. Clin Immunogenet 2000; 17:83-96.

Scaviner et al., The Human T Cell Receptor Alpha Variable (TRAV) Genes, Exp. Clin Immunogenet 2000; 17:97-106.

Szczepanski et al., "Ig heavy chain gene rearrangements in T-cell acute lymphoblastic leukemia exhibit predominant DH6-19 and DH7-27 gene usage, can result in complete V-D-J rearrangements, and are rare in T-cell receptor alpha beta lineage", *Blood*, vol. 93, No. 12, 1999: pp. 4079-4085.

Tomlinson et al., "The Repertoire of Human Germline $V_H$ Sequences Reveals about Fifty Groups of $V_H$ Segments with Different Hypervariable Loops", J. Mol. boil. (1992) 227, 776-708.

* cited by examiner

SEQUENCE LISTING

<160> NUMBER OF SEQ ID NOS: 20

<210> SEQ ID NO 1
<211> LENGTH: 22
<212> TYPE: DNA
<213> ORGANISM: Artificial
<220> FEATURE:
<223> OTHER INFORMATION: primer Vk3-20 Up

<400> SEQUENCE: 1
tctcaccatc agcagactgg ag                                              22

<210> SEQ ID NO 2
<211> LENGTH: 20
<212> TYPE: DNA
<213> ORGANISM: Artificial
<220> FEATURE:
<223> OTHER INFORMATION: Primer Intron Up1

<400> SEQUENCE: 2
ccgattaatg ctgccgtagc                                                 20

<210> SEQ ID NO 3
<211> LENGTH: 20
<212> TYPE: DNA
<213> ORGANISM: Artificial
<220> FEATURE:
<223> OTHER INFORMATION: primer Intron Up2

<400> SEQUENCE: 3
cccgattaat gctgccgtag                                                 20

<210> SEQ ID NO 4
<211> LENGTH: 19
<212> TYPE: DNA
<213> ORGANISM: Artificial
<220> FEATURE:
<223> OTHER INFORMATION: Primer Intron Up3

<400> SEQUENCE: 4
ggcaccgcga gctgtagac                                                  19

<210> SEQ ID NO 5
<211> LENGTH: 20
<212> TYPE: DNA
<213> ORGANISM: Artificial
<220> FEATURE:
<223> OTHER INFORMATION: Primer Kde Down2

<400> SEQUENCE: 5
cctagggagc agggaggctt                                                 20

<210> SEQ ID NO 6
<211> LENGTH: 27
<212> TYPE: DNA
<213> ORGANISM: Artificial
<220> FEATURE:
<223> OTHER INFORMATION: primer Kde Down3

<400> SEQUENCE: 6
cctcagaggt cagagcaggt tgtccta                                         27

<210> SEQ ID NO 7
<211> LENGTH: 24
<212> TYPE: DNA
<213> ORGANISM: Artificial

```
<220> FEATURE:
<223> OTHER INFORMATION: primer Kde Down4

<400> SEQUENCE: 7
tacagacagg tcctcagagg tcag                                              24

<210> SEQ ID NO 8
<211> LENGTH: 25
<212> TYPE: DNA
<213> ORGANISM: Artificial
<220> FEATURE:
<223> OTHER INFORMATION: primer Vk3-20 Down

<400> SEQUENCE: 8
ctatctgtaa aggaagcagc tggta                                             25

<210> SEQ ID NO 9
<211> LENGTH: 23
<212> TYPE: DNA
<213> ORGANISM: Artificial
<220> FEATURE:
<223> OTHER INFORMATION: primer Kde-germline Up

<400> SEQUENCE: 9
cttaccctag agtttctgca cgg                                               23

<210> SEQ ID NO 10
<211> LENGTH: 20
<212> TYPE: DNA
<213> ORGANISM: Artificial
<220> FEATURE:
<223> OTHER INFORMATION: primer Int-Kde BREC-F

<400> SEQUENCE: 10
tcagcgccca ttacgtttct                                                   20

<210> SEQ ID NO 11
<211> LENGTH: 17
<212> TYPE: DNA
<213> ORGANISM: Artificial
<220> FEATURE:
<223> OTHER INFORMATION: primer Int-Kde BREC R

<400> SEQUENCE: 11
gtgagggaca cgcagcc                                                      17

<210> SEQ ID NO 12
<211> LENGTH: 23
<212> TYPE: DNA
<213> ORGANISM: Artificial
<220> FEATURE:
<223> OTHER INFORMATION: probe Kde-RSS

<400> SEQUENCE: 12
acagtgtgcg ctgccaacct gct                                               23

<210> SEQ ID NO 13
<211> LENGTH: 29
<212> TYPE: DNA
<213> ORGANISM: Artificial
<220> FEATURE:
<223> OTHER INFORMATION: probe Kde-RSS_2

<400> SEQUENCE: 13
ccagctctta ccctagagtt tctgcacgg                                         29
```

```
<210> SEQ ID NO 14
<211> LENGTH: 20
<212> TYPE: DNA
<213> ORGANISM: Artificial
<220> FEATURE:
<223> OTHER INFORMATION: primer Kde Down1

<400> SEQUENCE: 14
ttcctaggga ggtcagactc                                          20

<210> SEQ ID NO 15
<211> LENGTH: 23
<212> TYPE: DNA
<213> ORGANISM: Artificial
<220> FEATURE:
<223> OTHER INFORMATION: primer Kde Down5

<400> SEQUENCE: 15
cccttcatag acccttcagg cac                                      23

<210> SEQ ID NO 16
<211> LENGTH: 33
<212> TYPE: DNA
<213> ORGANISM: Artificial
<220> FEATURE:
<223> OTHER INFORMATION: probe T-Kde

<400> SEQUENCE: 16
agctgcattt ttgccatatc cactatttgg agt                           33

<210> SEQ ID NO 17
<211> LENGTH: 19
<212> TYPE: DNA
<213> ORGANISM: artificial
<220> FEATURE:
<223> OTHER INFORMATION: coding joint sequence 1

<400> SEQUENCE: 17
ggcaccgcga gctgtagac                                           19

<210> SEQ ID NO 18
<211> LENGTH: 20
<212> TYPE: DNA
<213> ORGANISM: Artificial
<220> FEATURE:
<223> OTHER INFORMATION: coding joint sequence 3 (reverse)

<400> SEQUENCE: 18
ttcctaggga ggtcagactc                                          20

<210> SEQ ID NO 19
<211> LENGTH: 20
<212> TYPE: DNA
<213> ORGANISM: Artificial
<220> FEATURE:
<223> OTHER INFORMATION: Signal joint sequence 1

<400> SEQUENCE: 19
tcagcgccca ttacgtttct                                          20

<210> SEQ ID NO 20
<211> LENGTH: 17
<212> TYPE: DNA
```

```
<213> ORGANISM: Artificial
<220> FEATURE:
<223> OTHER INFORMATION: signal joint sequence 3 (reverse)

<400> SEQUENCE: 20
gtgagggaca cgcagcc                                                    17
```

DETERMINING THE REPLICATIVE HISTORY OF LYMPHOCYTES

CROSS-REFERENCE TO RELATED APPLICATIONS

This application is a continuation-in-part of PCT International Patent Application No. PCT/NL2005/000761, filed on Oct. 24, 2005 designating the United States of America, and published, in English, as PCT International Publication No. WO 2006/046860 A1 on May 4, 2006, which application claims priority to United States Provisional Patent Application Ser. No. 60/622,317, filed on Oct. 25, 2004, the contents of each of which are hereby incorporated herein by this reference.

TECHNICAL FIELD

The invention relates generally to the field of biotechnology, particularly immunology and immunodiagnostics. More specifically, the invention relates to a method for determining the replicative history of lymphocytes, such as B and T cells. A method of the invention is, among others, advantageously used to assess recovery of the (precursor) B-cell compartment in a patient following bone marrow transplantation.

BACKGROUND

Cells of the immune system arise from pluripotent stem cells through two main lines of differentiation: the lymphoid lineage that produces lymphocytes (T cells and B cells) and the myeloid lineage that produces phagocytes (monocytes, macrophages and neutrophils) and other cells. T cells and B cells are produced at a high rate (approximately $10^9$ per day) in the primary or central lymphoid organs, i.e., the thymus and bone marrow, respectively. These lymphocytes can migrate via the blood circulation into the secondary lymphoid organs (spleen, lymph nodes, tonsils, and mucosa-associated lymphoid tissue). B cells, or B lymphocytes, represent about 5 to 15% of the circulating lymphoid pool, and are classically defined by the presence of immunoglobulin molecules on their surface membrane. These immunoglobulin molecules are produced by the B cells themselves and are inserted into the surface membrane where they act as specific antigen receptors.[1, 2] Upon activation, B cells combat extracellular pathogens and their products by releasing immunoglobulins, which act as antibodies that specifically recognize and bind to a particular target molecule, called the antigen.

B-cell development, also known as B lymphopoiesis, in mouse and in man can be divided into two main phases, an antigen-independent phase of fresh production of precursor B cells in the bone marrow that mature into functional B lymphocytes and an antigen-dependent phase, in which the mature B lymphocyte compartment is maintained by regeneration, turnover and selection processes.[3] Once the immune system has been built, it contains around $5 \times 10^8$ and $10^{12}$ cells of the B lymphocyte lineage in the mouse and in man, respectively, of which 5 to 10% are precursor B cells that are active in continuous production of fresh B cells, whereas over 90% are mature B cells.

The many different B cells of the immune system each produce different immunoglobulin (Ig) molecules, which can specifically bind to a foreign antigen. These Ig molecules consist of two identical Ig heavy chains and two identical Ig light chains, Igκ or Igλ. The antigen-binding variable domains of the Ig chains differ per B cell and are encoded by different combinations of variable (V), diversity (D), and joining (J) gene segments in the case of Ig heavy chains and different combinations of V and J gene segments in the case of Igκ and Igλ chains.[4, 5] The many different V, D and J gene segments in the Ig heavy chains (IGH) gene and the many different V and J gene segments of the Igκ (IGK) and Igλ (IGL) genes determine the potential V(D)J combinatorial repertoire, which is estimated to consist of $>2 \times 10^6$ different Ig molecules in man (FIG. 1). During B-cell development in the bone marrow, precursor B cells form specific exons for the variable domains of antibody molecules by recombining individual V, D, and J gene segments via so-called gene rearrangement processes.[4] For example, in the IGH gene D to J rearrangement generally occur before V to D-J rearrangement, resulting in a specific V-D-J exon that can be transcribed into IGH mRNA and translated into IgH protein chains (FIG. 2). Comparable V-(D-)J rearrangement processes occur in IGK and IGL genes as well as in the T-cell receptor (TCR) genes, which encode the antigen-recognizing TCR molecules of T cells. [4, 6]

All V, D, and J gene segments are flanked by specific homologous recombination signal sequences (RSS).[7] These RSS consist of a conserved palindromic heptamer sequence (CACAGTG) adjacent to the coding sequence and a conserved nonamer sequence (ACAAAAACC) that are separated by a less conserved spacer region of either 12 or 23 base pairs (bp). In principle, only RSS of different spacer length join efficiently, known as the so-called 12/23 rule (FIG. 3). However, sometimes incomplete RSS, only consisting of a heptamer, are used. RSS are recognized by recombination activation gene 1 and 2 proteins (RAG1 and RAG2), which are able to cleave the DNA between the heptamer and the coding end of the involved gene segment. [8, 9] The DNA cleavage results in a hairpinned coding end and a blunt 5-phosphorylated signal end. A so-called coding joint is obtained after cleavage and ligation of the hairpinned coding ends. During this ligation process, further (junctional) diversity of the coding joints is obtained by deletion and insertion of nucleotides, resulting in a highly diverse junctional region.[10] The V-(D-)J exon with the junctional region together with the constant exons are transcribed into mRNA and translated into protein (FIG. 2). The signal ends are also ligated and thereby form an extrachromosomal circular excision product containing the two coupled RSS, which is referred to as the signal joint (FIG. 2).

The extrachromosomal (episomal) excision product of the Ig gene rearrangement is also called "B-cell receptor excision circle" (BREC). These episomal products cannot replicate in the cell and appear to be highly stable structures, which can persist for a significant length of time. Consequently, BRECs can be found not only in precursor B cells but also in mature B lymphocytes. The role of the excision products in mature B cells is not fully clear.

During B-cell differentiation in bone marrow, the IGH genes and one of the Ig light chain genes (IGK or IGL) have to rearrange functionally in order to produce a complete Ig molecule. IGH gene rearrangements (D to J, followed by V to D-J) precede the Ig light chain gene rearrangements with IGK gene rearrangements occurring prior to IGL gene rearrangements (FIG. 4).[11, 12] Functional IGK gene rearrangements result in Igκ producing B cells that usually retain their IGL genes in germline configuration.[13, 14] If the IGK gene rearrangements are not functional, the IGL genes rearrange in an attempt to produce Igλ+ B cells. Interestingly, most Igλ-producing B cells have deleted their IGK genes on at least one allele, generally on both alleles (FIG. 4).[14, 15]

IGK gene deletions are mediated via rearrangement of the so-called kappa-deleting element (Kde), which is located approximately 24 kb downstream of the constant (C) kappa gene segment (Cκ).[16-19] Kde can either rearrange to a heptamer RSS in the intron between the Jκ and Cκ gene segments (intronRSS) or to one of the available Vκ gene segments (FIG. 5). The intronRSS-Kde rearrangement deletes the Cκ gene segment, whereas Vκ-Kde rearrangements delete the complete Jκ-Cκ region. Both types of Kde rearrangements also delete the two enhancers of the IGK locus (iEκ and 3'Eκ) implying that Kde rearrangements are "end-stage" rearrangements, precluding any further rearrangement in the IGK locus (FIG. 5).[20] The Kde rearrangements are found in precursor B cells and in mature B cells, particularly in (virtually) all Igλ+ mature B cells.[21-23] Also, a part of the Igκ+ B cells contain Kde rearrangements, but they are absent in the majority of Igκ+ B cells.[14, 22]

It will be understood that B-cell development is important during health and disease. Dysfunction of the precursor B-cell compartment or the mature B-cell compartment is observed in various types of immune diseases, during immunosuppressive treatments (e.g., with cyclosporin), during cancer treatment,[24, 25] and following bone marrow transplantation (BMT).[26] Furthermore, B-cell development is typically reduced during aging.[27]

BMT and peripheral blood stem cell transplantation (PBSCT) are procedures that aim at restoration of the stem cell compartment, when it is affected by specific diseases (e.g., primary immunodeficiencies, cancer, etc.) and/or when it has been destroyed by high doses of chemotherapy and/or radiation therapy. Generally speaking, the goal is to replace the diseased marrow with healthy bone marrow. Bone marrow is mainly concentrated in the skull, ribs, sternum, vertebrae and pelvic bone, and less so in other bones. It contains immature hematopoietic cells called hematopoietic stem cells that produce blood cells. Most stem cells are found in the bone marrow, but some stem cells called peripheral blood stem cells (PBSCs) can be found in the bloodstream. Stem cells can divide to form more stem cells, or they can mature into white blood cells, red blood cells, or platelets. In cancer treatment, the main purpose of BMT and PBSCT is to make it possible for patients to receive very high doses of chemotherapy and/or radiation therapy. Chemotherapy and radiation therapy generally affect cells that divide rapidly, including bone marrow cells. BMT and PBSCT replace stem cells that were destroyed by treatment. The healthy, transplanted stem cells can restore the bone marrow's ability to produce the blood cells the patient needs. After entering the bloodstream, the transplanted cells travel to the bone marrow, where they begin to produce new white blood cells, red blood cells, and platelets in a process known as "engraftment."

A major problem in the field of transplantation, be it BMT or PBSCT, is the difficulty to monitor the efficacy of transplantation and, herewith, to determine the optimal treatment protocol. Evaluation of B-cell-dependent antibody production is one way to determine how well the new bone marrow is working. However, it is very difficult to obtain direct insight into the origin of B cells in the transplanted recipient. This is because after BMT or PBSCT, B cells can, in theory, regenerate from several sources: (1) mature B cells of the transplant recipient which survived the pre-transplantation chemotherapeutic intensification treatment; such cells may be seeded in the bone marrow, lymph nodes, or spleen; (2) mature B cells present in the graft; (3) hematopoietic stem cell progenitors in the transplant that differentiate after grafting in the recipient; and (4) residual recipient stem cells. Thus, given the various possible B cell sources, serotyping does not allow discrimination between antibodies produced by newly developed B cells and antibodies produced by old mature B cells that have expanded in the periphery of the recipient. If the antibody production is solely based on expanding mature B cells (not on newly produced B cells as well), antibody production will end . as the old B cells die off. Rather, the efficacy of regeneration of the precursor B-cell compartment should ideally be monitored by determining the "age" of the B cells present in a subject, allowing distinguishing between newly produced B cells and "old" B cells.

SUMMARY OF THE INVENTION

The present invention now provides insight that detection of extrachromosomal excision products of the Ig gene rearrangement allows discrimination between immature and mature subsets of B cells, for instance, between recently produced (immature) B cells and expanded B cells, such as long-lived memory B cells.

Provided is a method for determining the replicative history of a lymphocyte, the method comprising detecting a signal joint nucleotide sequence on an extrachromosomal circular excision product in the lymphocyte, wherein the excision product is deleted from a chromosome to give a chromosomal-coding joint nucleotide sequence that is retained in the chromosome and detecting the coding joint nucleotide sequence in the lymphocyte. Preferably, the coding joint is present in a significant subset of the lymphocytes (e.g., in 0.1 to 80% of the cells, preferably in 5% to 50% of the cells).

The underlying concept of a method according to the invention is based on the principle that with each round of replication, the chromosomal-coding joint nucleotide sequence in a lymphocyte is replicated whereas the episomal circular excision product carrying the signal joint nucleotide sequence remains intact yet is not replicated. Consequently, with each round of replication of a lymphocyte, the episomal products are diluted during division such that the coding/signal joint ratio increases (see FIG. 6). Whereas the invention will be primarily illustrated using B cells, it is to be understood that the invention may also be suitably used for determining the replicative history of a T cell, provided that suitable signal and coding joint nucleotide sequences are chosen for detection (see further below).

The underlying concept of a method according to the invention is based on the principle that with each round of replication, the chromosomal-coding joint nucleotide sequence in a lymphocyte is replicated whereas the episomal circular excision product carrying the signal joint nucleotide sequence remains intact yet is not replicated. Consequently, with each round of replication of a lymphocyte, the episomal products are diluted during division such that the coding/signal joint ratio increases (see, FIG. 6). Whereas the invention will be primarily illustrated using B cells, it is to be understood that the invention may also be suitably used for determining the replicative history of a T cell, provided that suitable signal and coding joint nucleotide sequences are chosen for detection (see further below).

In a preferred embodiment, a method of the invention further comprises calculating the ratio between the chromosomal-coding joint nucleotide sequence and the extrachromosomal signal joint nucleotide sequence. The higher the ratio, the more cell divisions the cell has undergone. Obviously, this principle requires that the coding joint nucleotide sequence remains chromosomal and that it is not removed by a subsequent gene rearrangement, i.e., it should be the result of a final (also called "end-stage") gene rearrangement. Detection of the coding joint sequence in the case of a non-final rearrangement would not provide useful quantitative information, because this coding joint sequence could be present on an extrachromosomal excision circle.

The occurrence of extrachromosomal-coding joint sequences is illustrated by a study reporting the use of episomal T cell receptor excision circles (TRECs) as markers for recent thymic emigrants.[28, 29] It was demonstrated that the frequently occurring TCR delta (TCRD) deletion rearrangement of δREC-ψJα in T cells results in an easily detectable TREC, containing the δREC-ψJα signal joint,[30] which can be quantified via real-time quantitative (RQ) polymerase chain reaction (PCR).[28, 29] Of course, also in this case, the δREC-ψJα rearrangement results in a chromosomal-coding joint. However, this coding joint is immediately removed upon subsequent Vα-Jα rearrangement and, therefore, cannot serve as an internal control or reference.[29] Thus, recently produced naïve T cells and expanded (memory) T cells can only be distinguished based on the TREC content.[29] Normalizing the extrachromosomal TREC content to the resulting chromosomal-coding joint sequence was not possible, because the TCRD deletion rearrangement is not an end-stage rearrangement.[29] In theory, a Vα-Jα rearrangement might be used in a method of the invention for detection of a TREC with the Vα-Jα signal joint and the corresponding chromosomal Vα-Jα coding joint. However, the high number of different Vα-Jα combinations (approximately 56×61≈3300) make Vα-Jα unattractive targets for detection. Furthermore, Vα-Jα rearrangements can be replaced by upstream Vα to downstream Jα rearrangements (Vα-Jα replacement rearrangements).

In a preferred embodiment, a method according to the invention comprises determining the replicative history of a B cell. To ensure that a major subset of B cells is covered by the detection method according to the invention, it is preferred that the signal joint sequence and the coding joint sequence arise from a frequently occurring Ig gene rearrangement. Moreover, this gene rearrangement preferably produces a single or only a few different types of excision circles, which can easily be detected. A suitable rearrangement to be detected in a method of the invention is preferably a frequently occurring "end-stage" rearrangement, i.e., a rearrangement that is not replaced or removed by a subsequent gene rearrangement.

For studying proliferation of early precursor B cells, only IGH gene rearrangements can be used, because other rearrangements are not yet present. For this purpose, a selected DH-JH or preferably a VH-DH can be used. This approach is typically sufficient to evaluate pre-B-cell receptor- (pre-BCR-) induced proliferation in the pre-B-II stage. Theoretically, IGH gene rearrangements can also be used for studying B-cell proliferation in later phases of B-cell differentiation/maturation. However, from the pre-B-II stage onwards, IGK gene rearrangements are more attractive targets, because the BRECs (B-cell receptor excision circles) of IGK gene rearrangements will only be diluted by cell divisions of mature peripheral B cells (FIG. 4). Of particular interest is the IGK deletion rearrangement, mediated via Kde rearrangement (FIG. 5). In a preferred embodiment, a method provided herein detects the products of a Kde rearrangement, comprising the detection of a signal joint nucleotide sequence on a Kde rearrangement excision circle (KREC), and detection of the corresponding coding joint nucleotide sequence on the rearranged chromosome. Kde rearrangements either delete the Cκ region or the complete Jκ-Cκ region, via rearrangement to the intronRSS or via rearrangement to a Vκ gene segment, respectively (FIG. 5). Accordingly, two main types of KRECs can be produced during a Kde rearrangement. The first results from the intronRSS to Kde rearrangement and the second results from a Vκ to Kde rearrangement. Because a Vκ to Kde rearrangement involves rearrangement of one of the multiple Vκ gene segments (approximately 76 different rearrangable Vκ gene segments), the resulting type of coding joint sequence and signal joint sequence depends on the particular Vκ gene segment involved. For example, a method of the invention comprises the detection of the chromosomal Vκ3.20-Kde-coding joint and the corresponding signal joint in a KREC. Many other Vκ-Kde rearrangements can be chosen as target, but they all occur in relatively small subsets of B cells.

In contrast, during the intronRSS to Kde rearrangement, only one type of coding joint sequence and one signal joint sequence can be formed. A method of the invention preferably comprises the detection of the intronRSS to Kde rearrangement, since this only requires one set of detection probes (e.g., nucleic acid amplification primers) for detection of the chromosomal-coding joint nucleotide sequence and one set of probes for detection of the signal joint nucleotide sequence, located on the KREC (FIG. 7).

Detection of a signal joint nucleotide sequence and a coding joint nucleotide sequence in a method of the invention can be performed using conventional molecular biological procedures. Preferably, it involves PCR analysis, more preferably RQ-PCR analysis. RQ-PCR permits accurate quantitation of PCR products during the exponential phase of the PCR amplification process, which is in full contrast to the classical PCR end point quantitation. Owing to the real-time detection of fluorescent signals during and/or after each subsequent PCR cycle, quantitative PCR data can be obtained in a short period of time and no post-PCR processing is needed, thereby drastically reducing the risk of PCR product contamination. RQ-PCR technology, for example, can use an ABI Prism 7700 instrument (TaqMan®) to detect accumulation of PCR products continuously during the PCR process, thus allowing easy and accurate quantitation in the early exponential phase of PCR. The ABI Prism 7700 uses fiber optic systems, which connect to each well in a 96-well PCR tray format. A laser light source excites each well and a CCD camera measures the fluorescence spectrum and intensity from each well to generate real-time data during the PCR amplification process. The ABI 7700 Prism software examines the fluorescence intensity and calculates the increase in intensity over the course of the amplification. The results are then plotted versus time, represented by cycle number, to produce a continuous measure of PCR amplification. To provide precise quantification of the initial target in each PCR, the amplification plot is examined at a point during the early log phase of product accumulation. This is accomplished by assigning a fluorescence threshold above background and determining the PCR cycle at which each sample's amplification plot reaches the threshold (defined as the threshold cycle number or CT).

At present, three main types of RQ-PCR techniques are available. In one embodiment of the invention, detection is based on detection of PCR products by the intercalating dye SYBR Green I. This dye can bind to the minor groove of double-stranded DNA, which greatly enhances its fluorescence. During the consecutive PCR cycles, the amount of double-stranded PCR product will exponentially increase and, therefore, more SYBR Green I dye can bind and emit its fluorescence (at 520 nm). It should be noted that SYBR Green I-based detection of PCR products is not sequence specific and that consequently, non-specifically amplified PCR products and primer dimers will also be detected. In addition to SYBR-Green I, other dyes can also be used in non-specific detection systems such as Amplifluor.

In a preferred embodiment, a method of the invention comprises detection and quantitation of a chromosomal-coding joint nucleotide sequence and of an extrachromosomal signal joint nucleotide sequence, preferably resulting from a Kde rearrangement, more preferably an intronRSS to Kde rearrangement. For example, RQ-PCR with hydrolysis probes is used. This type of RQ-PCR exploits the 5'→3' exonuclease activity of the *Thermus aquaticus* (Taq) polymerase to detect and quantify specific PCR products as the reaction proceeds. The hydrolysis probe, also referred to as TaqMan® probe or double-dye oligonucleotide probe, is conjugated with a reporter (R) fluorochrome (e.g., FAM, VIC or JOE) as well as a quencher (Q) fluorochrome (e.g., TAMRA) and should be positioned within the target sequence (see FIG. 7). The quencher fluorochrome absorbs the fluorescence of the reporter fluorochrome as long as the probe is intact. However, upon amplification of the target sequence, i.e., the signal joint or the coding joint sequence, the hydrolysis probe is displaced and hydrolyzed by the Taq polymerase. This results in the separation of the reporter and quencher fluorochrome and consequently the fluorescence of the reporter fluorochrome becomes detectable. During each consecutive PCR cycle, this fluorescence will further increase because of the progressive and exponential accumulation of free reporter fluorochromes.[31, 32]

In yet a further embodiment, RQ-PCR using hybridization probes is used for the detection and quantitation of a signal joint sequence and a coding joint sequence of interest in a B cell, such that the replicative history of the B cell can be determined. RQ-PCR analysis with hybridization probes uses two juxtaposed sequence-specific probes, one labeled with a donor fluorochrome (e.g., FAM) at the 3' end and the other labeled with an acceptor fluorochrome (e.g., LC Red640, LC Red705) at its 5' end. Both probes should hybridize to closely juxtaposed target sequences on the amplified DNA fragment, thereby bringing the two fluorochromes into close proximity (preferably within 1 to 5 nucleotides) such that the emitted light of the donor fluorochrome will excite the acceptor fluorochrome. This results in the emission of fluorescence, which can be detected during the annealing phase and the first part of the extension phase of the PCR reaction. After each subsequent PCR cycle, more hybridization probes can anneal, resulting in higher fluorescence signals.

In addition to the three main RQ-PCR approaches described above, other types of probes may also be used in a method provided herein, including molecular beacons, Scorpions, minor groove-binding (MGB) probes, Reson-Sense, Hy-Beacon, and Light-up probes.[33]

In another aspect, the invention provides a set of at least two pairs of nucleic acid amplification primers comprising at least a first pair of primers for detecting a signal joint nucleotide sequence on an extrachromosomal circular excision product in a lymphocyte and a second pair of primers for detecting a corresponding chromosomal-coding joint nucleotide sequence in a lymphocyte, preferably wherein the lymphocyte is a B cell.

In one embodiment, such a set comprises a pair of primers for detecting a signal joint nucleotide sequence on a kappa-deleting element rearrangement excision circle (KREC) and/or a pair of primers for detecting a coding joint derived from a Kde rearrangement, preferably an intronRSS-Kde rearrangement. Suitable primers and probes used in a method of the invention are set out in Table 1.

In a specific embodiment, the invention provides a nucleic acid amplification primer selected from the group of oligonucleotides consisting of:

```
                                      (SEQ ID NO: 1)
5'-TCTCACCATCAGCAGACTGGAG-3' (Vk3-20 Up), (SEQ ID NO: 2)
5'-CCGATTAATGCTGCCGTAGC-3' (Intron Up1), (SEQ ID NO: 3)
5'-CCCGATTAATGCTGCCGTAG-3' (Intron Up2), (SEQ ID NO: 4)
5'-GGCACCGCGAGCTGTAGAC-3' (Intron Up3), (SEQ ID NO: 5)
5'-CCTAGGGAGCAGGGAGGCTT-3' (Kde Down2), (SEQ ID NO: 6)
5'-CCTCAGAGGTCAGAGCAGGTGTCCTA-3' (Kde Down3), (SEQ ID NO: 7)
5'-TACAGACAGGTCCTCAGAGGTCAG-3' (Kde Down4), (SEQ ID NO: 8)
5'-CTATCTGTAAAGGAAGCAGCTGGTA-3' (Vk3-20 Down), (SEQ ID NO: 9)
5'-CTTACCCTAGAGTTTCTGCACGG-3' (Kde-germline Up), (SEQ ID NO: 10)
5'-TCAGCGCCCATTACGTTTCT-3' (Int-Kde BREC F),
and (SEQ ID NO: 11)
5'-GTGAGGGACACGCAGCC-3' (Int-Kde BREC R)
```

(see Table 1), or a variant thereof. Also provided herein is a set of primers comprising at least one of the primers selected from the group consisting of primers Vk3-20 Up, Intron Up1, Intron Up2, Intron Up3, Kde Down2, Kde Down3, Kde Down4, Vk3-20 Down, Kde-germline Up, Int-Kde BREC F and Int-Kde BREC R (see Table 1 for nucleotide sequence of these primers, or a variant thereof. Very good results can be obtained with primers Intron Up2 and/or Kde Down2 and/or Int-Kde BREC F and/or Int-Kde BREC R in RQ-PCR-based detection of corresponding coding and signal joints of Kde rearrangements and germline Kde alleles.

The term "variant" refers to a primer that differs in 1 to 5 nucleotides, preferably 1 to 3 nucleotides, more preferably 1 to 2 nucleotides from the size and/or position from the nucleotide of a primer sequence shown in Table 1, provided that the nucleotide sequence of the variant primer contains at most two mismatches, preferably at most one mismatch, most preferably no mismatches with the target sequence and that the variant primer hybridizes with the target nucleotide sequence. In addition, a variant primer comprises a (differentially) labeled primer, i.e., a primer having a label that can be identified or distinguished from other labels by any means, including the use of an analytical instrument. Examples of differentially labeled primers are primers provided with a fluorescent label such as a 6-FAM, HEX, TET or NED dye.

In another aspect of the invention, a nucleic acid amplification assay, preferably a PCR assay, more preferably a RQ-PCR assay, is provided using a set of primers as provided herein. For example, a two tube PCR assay is provided wherein one tube comprises a set of a forward and a reverse primer for amplification of a coding joint sequence of an end-stage rearrangement in a B cell and wherein another tube comprises a set of a forward and a reverse primer for amplification of the corresponding extrachromosomal excision circle, preferably KREC. Also provided are oligonucleotide probes homologous to an internal sequence of an amplified nucleic acid sequence (amplicon) produced in a nucleic acid amplification assay according to the invention to detect and quantify such an amplicon. These probes may be non-specific or sequence-specific, and they may be provided with at least one, preferably two fluorochromes, such as hydrolysis probes or hybridization probes. Examples of useful sequence-specific probes are depicted in Table 1 and FIG. 7. In a specific aspect, the invention provides probe Kde-RSS or probe T-Kde-RSS_2 having nucleotide sequence 5'-ACAGTGTGCGCTGCCAACCTGCT-3' (SEQ ID NO:12) and 5'-CCAGCTCTTACCCTAGAGTTTCTG-CACGG-3' (SEQ ID NO:13), respectively (see Table 1). Very good results can be obtained using probe T-Kde-RSS_2. These probes, or variants thereof (for definition of the term "variant" see above), are advantageously used to detect and quantify the coding joint nucleotide sequence and the signal joint nucleotide sequence in a B cell, such that the ratio can be calculated between the chromosomal (replicating) and the extrachromosomal (non-replicating) sequence.

Importantly, the invention also provides a cell (or a culture or stock thereof), that can be used as a positive control in a method of the invention. This cell line is stably transformed (e.g., by using retroviral gene transduction) with one copy of a nucleic acid sequence comprising a signal joint nucleotide sequence of an extrachromosomal circular excision product that can be present in a lymphocyte. In a preferred embodiment, the lymphocyte is a B cell. More preferably, the extrachromosomal circular excision product is a KREC. This "control" cell line also contains a nucleic acid sequence comprising a coding joint nucleotide sequence that is formed as the result of the deletion of the excision product, preferably a coding joint sequence resulting from an intronRSS to Kde rearrangement. In contrast to the cells to be tested, the coding joint and the signal joint sequences that are present in a control cell line according to the invention are both replicated during cell division. Consequently, the ratio between the two can be set at 1.0. A control cell as provided herein not only serves as an internal control for the ratio between the coding joint and signal joint sequence, but also as 100% setting for the (RQ)-PCR reactions that are performed to detect and quantify the presence of the coding joint and signal joint sequences in a B cell or B-cell population.

Preferably, the control cell line also contains a Kde sequence in germline configuration, which can serve as control for IGK alleles without a deletional rearrangement. This control information might be relevant for interpretation of results in B-cell populations with low levels of intronRSS-Kde rearrangements. Normal B cells have two IGK alleles and the Kde sequence in the IGK locus can occur in three different configurations: germline Kde, intron RSS-Kde rearrangement, Vκ-Kde rearrangement, which together should represent a "100% signal" in RQ-PCR assays. Consequently, it is possible to estimate the amount of Vκ-Kde rearrangement in a B-cell population by the following formula: % Vκ-Kde=100% −(% germline Kde+% intron RSS-Kde). The presence of a germline Kde allele can be quantified with the same oligonucleotide set as used for the intronRSS-Kde-coding joint sequence (see Table 1 and FIG. 7), but using a different upstream primer, for example, 5'-GTGAGGGACACGCAGCC-3' (Primer Int-Kde BREC R) (SEQ ID NO:20).

A diagnostic kit is provided comprising the means for carrying out a method according to the invention. A diagnostic kit, for instance, comprises at least one, preferably at least two, nucleic acid amplification primer selected from primers Vk3-20 Up, Intron Up1, Intron Up2, Intron Up3, Kde Down2, Kde Down3, Kde Down4, Vk3-20 Down, Kde-germline Up, Int-Kde BREC F and Int-Kde BREC R (see, Table 1 for nucleotide sequence of these primers) or a primer set according to the invention. Such a kit comprises, for example, a set of nucleic acid amplification primers for amplification of a chromosomal-coding joint sequence and a primer set for amplification of an extrachromosomal signal joint sequence. Preferably, the kit further contains one or more detection probes for detecting the amplified sequence, for example, a TaqMan probe, which allows detection and quantitation of intronRSS-Kde-coding joint sequences and/ or a probe for detection and quantitation of KRECs containing the corresponding signal joint sequence, for example, probe Kde-RSS and/or probe T-Kde-RSS_2. Furthermore, a kit of the invention may comprise a control cell according to the invention.

In a specific embodiment, a kit of the invention comprises the primer Intron Up2, primer Kde Down2, probe T-Kde, preferably in combination with primers Int-Kde BREC F and Int-Kde BREC R and probe T-Kde-RSS_2.

In one embodiment, use of a method according to the invention is provided to determine the age or replicative history of a normal or a diseased B cell, wherein the B cell is preferably selected from the group consisting of bone marrow precursor B cell, neonatal cord blood B cell, childhood peripheral blood B cell, adult peripheral blood B cell, tonsil B cell, lymph node B cell, as well as specific subsets of B cells, such as precursor B-cell subsets, virgin B-cell subsets, memory B-cell subsets, B-cell subsets with or without IgH class switch, germinal center B cells and plasma cells. A method as provided herein is particularly suitable to assess bone marrow function in a subject, for example, a subject that has received a BMT. The method can also be used to compare the replicative history of different B-cell subsets of the same individual or the same patient in order to understand disrupted B-cell differentiation and B-cell maturation in specific disease states.

In another aspect, a method of the invention is used to evaluate the efficiency of vaccination in a human or animal. For example, in the process of monoclonal antibody production, the response to an antigen can be determined.

Furthermore, a method is advantageously used to monitor the B-cell status in relation to age and age-related diseases. Immune system alterations during aging are complex and pleiotropic, suggestive of remodeling or altered regulation, rather than simple immune deficiency. Evidence suggests that changes in the immune system may be involved in some major age-related pathologies, such as atherosclerosis and Alzheimer's disease. Normal mice and man exhibit reduced development of B lymphocytes in senescence ("old age") and decreased antibody-mediated immunity. Research indicates that in senescent mice, the production of B lymphocytes is abnormally regulated at a precise developmental stage: the pre-B cell. Studies have revealed a decline in the expression of molecules critical to the establishment of pre-B cells, including the surrogate light chains, which comprise the pre-B-cell receptor. Newly formed pre-B cells express pre-B-cell receptor (pre-BCR) molecules at the cell surface. These pre-BCR molecules are comprised of the IgH together with surrogate light chain proteins. Signaling via the pre-BCR promotes survival and proliferation of the newly produced pre-B cells. In aged mice, production of surrogate light chains is reduced, presumably affecting pre-BCR expression and/or function. This, in turn, may result in decreased production of pre-B cells and B cells. A method of the invention to determine the replicative history of a B cell is obviously useful for studying the cellular and molecular mechanisms, which lead to dysregulated B-cell development in senescence and the molecular defects, which are responsible.

The invention is exemplified by the experiments below, which describe methods for real-time quantitative PCR detection of $K_{de}$ rearrangement excision circles (KRECs) in (precursor) B-cell subsets.

DETAILED DESCRIPTION OF THE INVENTION

Experimental Section

Figure 1:
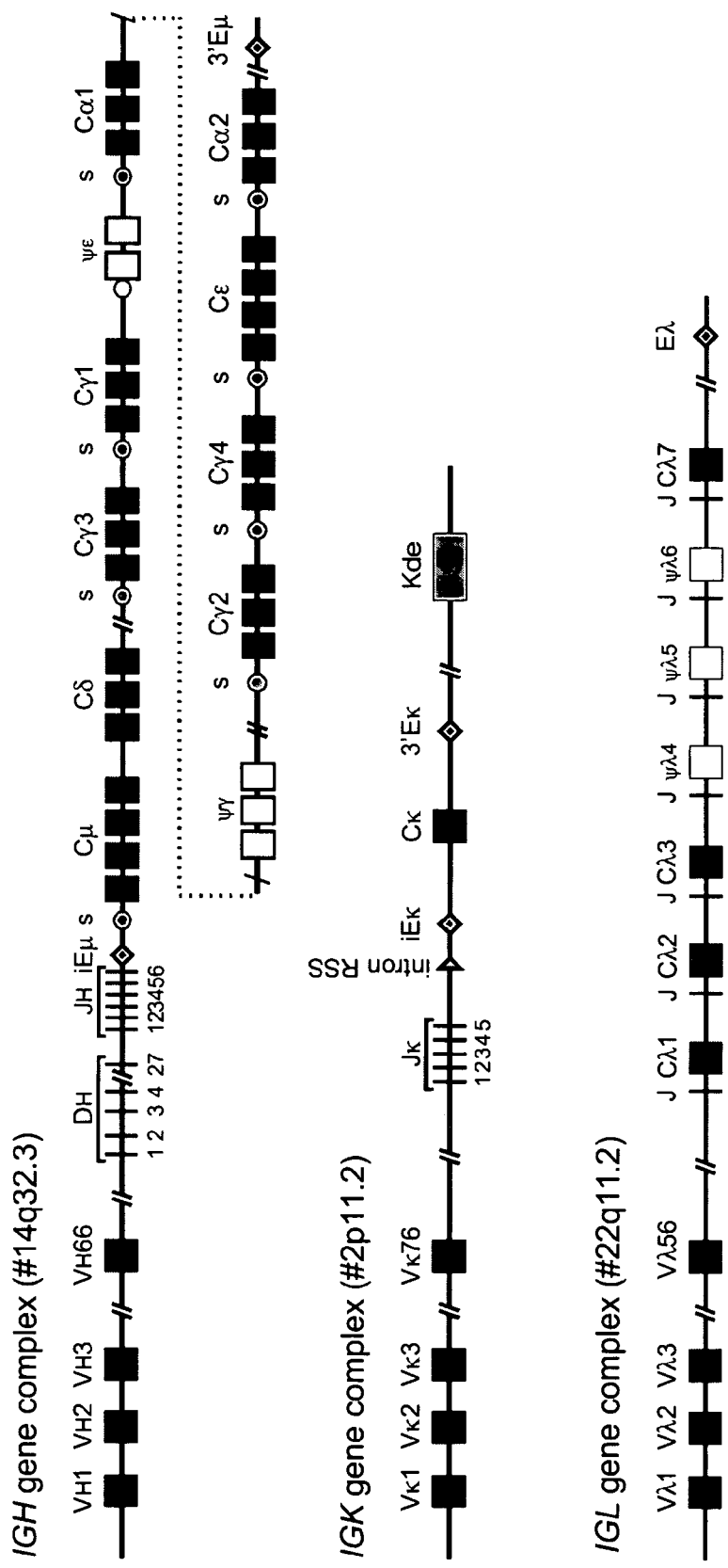
FIG. 1: Schematic diagram of the human Ig gene complexes. The IGH gene complex consists of at least 40 functional VH gene segments, 27 DH gene segments, six functional JH gene segments, and several CH gene segments, which together encode the various IgH class and subclass constant domains. Most CH gene segments are preceded by a switch gene(s), which plays a role in IgH (sub)class switch. The IGK gene complex consists of approximately 35 functional Vk gene segments, five Jk gene segments, and a single Ck gene segment. The downstream located Kde (kappa-deleting element) plays a role in the deletion of the Jk-Ck or Ck gene regions in B cells, which rearrange their IGL genes. The IGL gene complex consists of approximately 30 functional Vl gene segments and four functional Cl gene segments, all of which are preceded by a Jl gene segment. Pseudo genes (ψ) are indicated as open symbols. The positioning of the enhancer (E) elements is indicated.
Figure 2:
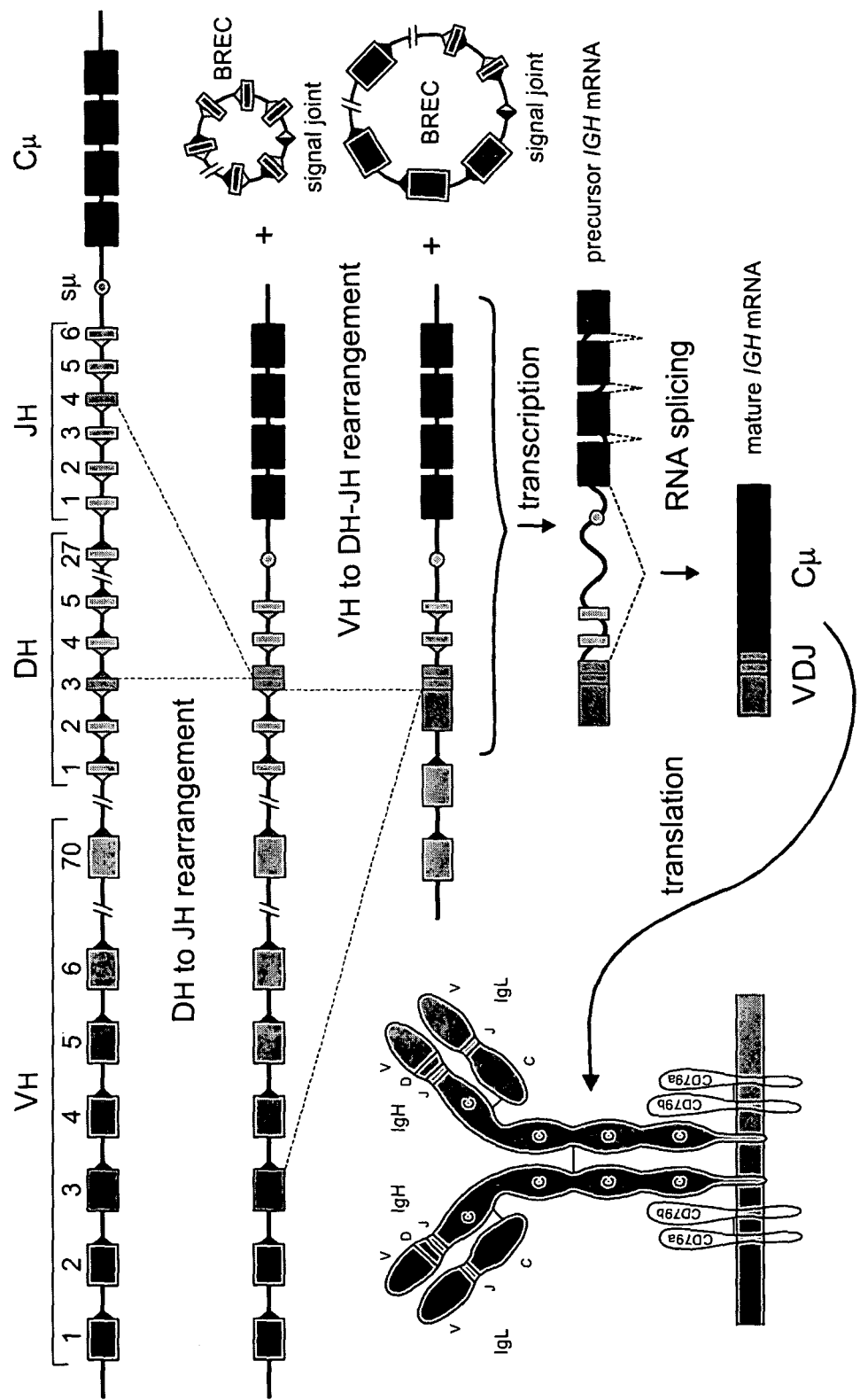
FIG. 2: Schematic diagram of sequential rearrangement steps, transcription, and translation of the IGH gene. In this example, first a DH to JH rearrangement occurs, followed by VH to DH-JH rearrangement, resulting in the formation of a VH-DH-JH exon with a junctional region, which contains two coding joints. The rearranged IGH gene is transcribed into precursor mRNA, spliced into mature mRNA, and finally translated into IgH protein. The two extrachromosomal B-cell receptor excision circles (BRECs) that are formed during this recombination process are depicted as well; they contain the D-J signal joint and V-D signal joint, respectively.
Figure 3:
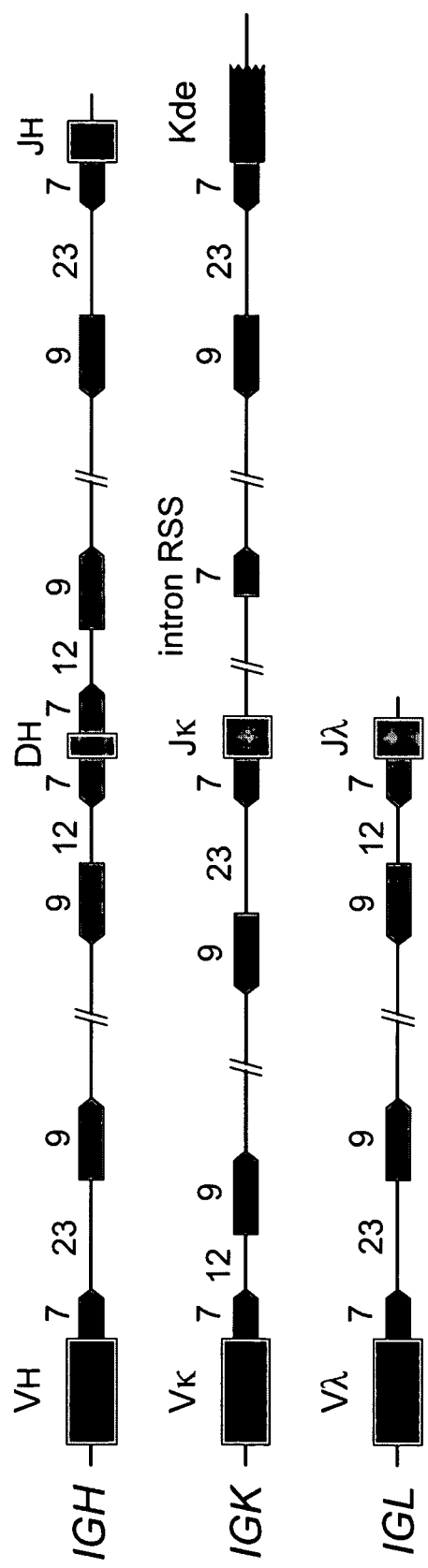
FIG. 3: Recombination signal sequences of human Ig genes. The vast majority of functional RSS consist of a conserved palindromic heptamer sequence adjacent to the coding sequence and a conserved nonamer sequence that are separated by a less conserved spacer region of either 12 or 23 base pairs (bp). In principle, only RSS of different spacer lengths join efficiently, known as the so-called 12/23 rule. Sometimes an incomplete RSS, only consisting of a heptamer, appears to be functional as well. For example, the so-called intronRSS in the IGK locus consists of a heptamer sequence only.
Figure 4:
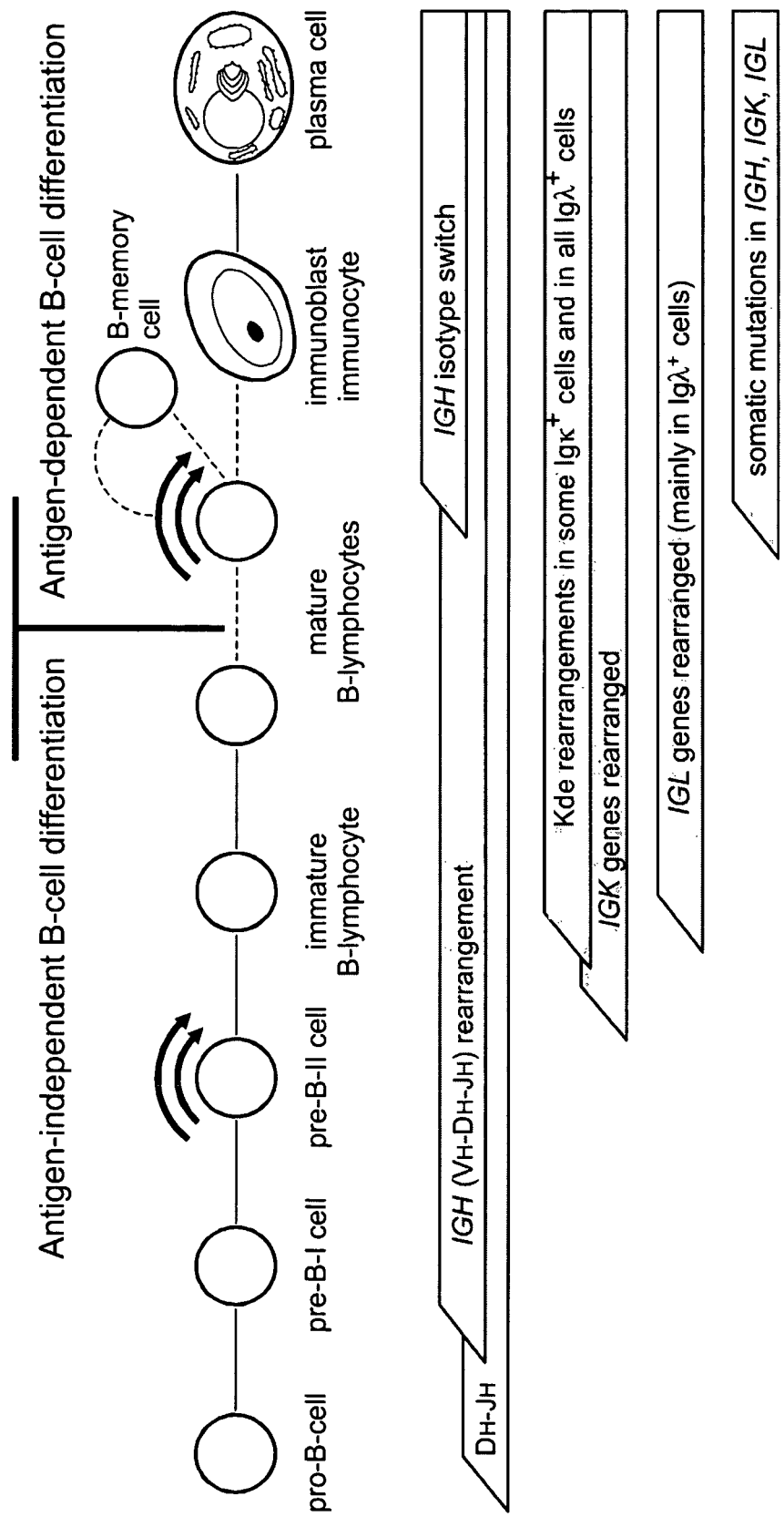
FIG. 4: Schematic diagram of human B-cell development and the hierarchical order of Ig gene rearrangement processes. Two main phases of B-cell development are indicated, an antigen-independent phase of fresh production of precursor B cells in the bone marrow that mature into functional B lymphocytes and an antigen-dependent phase, in which the mature B-lymphocyte compartment is maintained by regeneration, turnover and selection. The consecutive steps of Ig gene rearrangements (antigen-independent phase), as well as IGH class switch and somatic hypermutation processes (antigen-dependent phase), are indicated.
Figure 5:
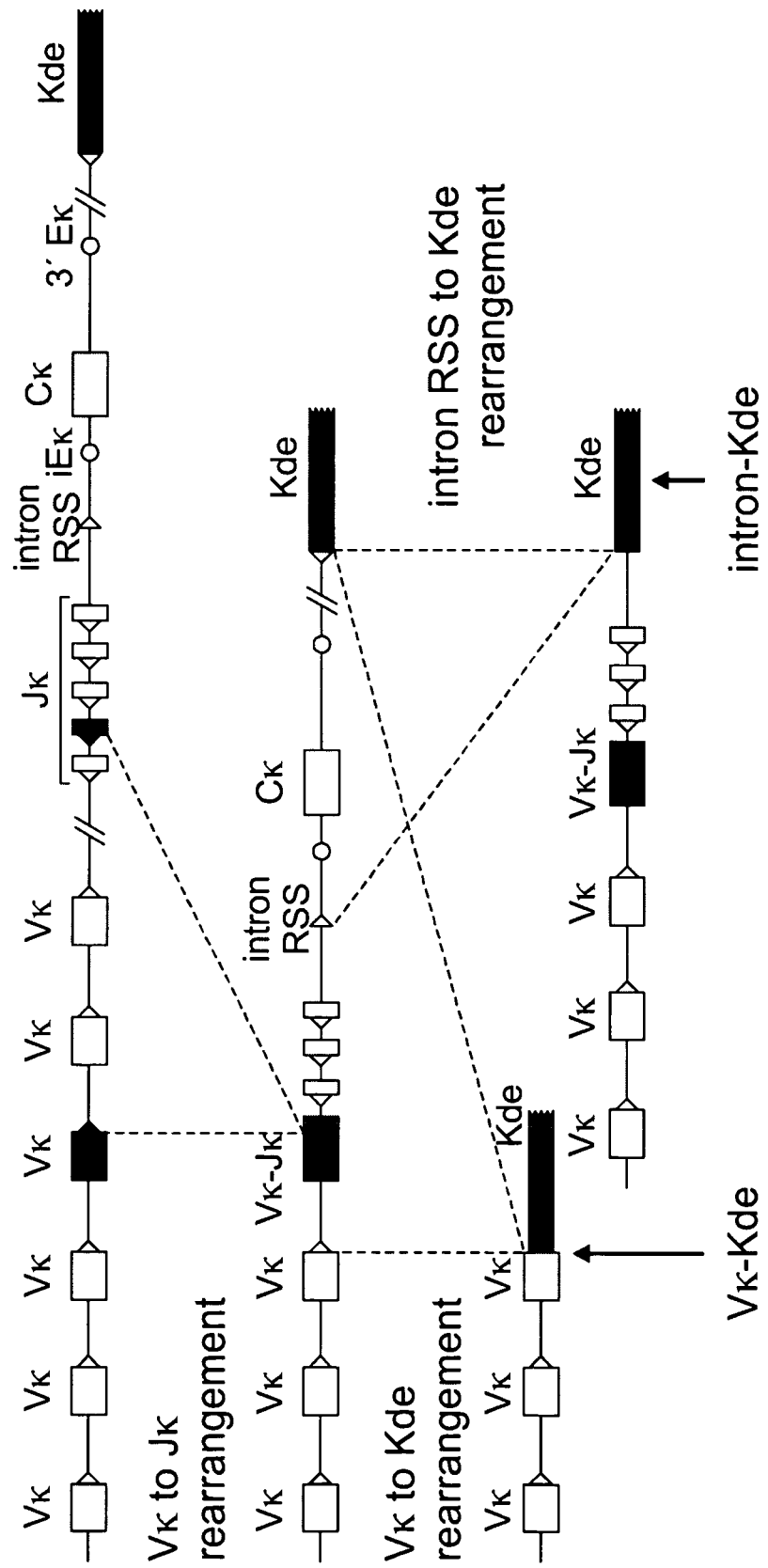
FIG. 5: Consecutive rearrangements in the IGK locus, resulting in the two main types of Kde rearrangements. Generally, recombination in the IGK locus starts with Vk-Jk rearrangement. Expression of the Vk-Jk rearranged allele can be disrupted by rearrangement of Kde (kappa-deleting element) to an intronRSS, resulting in deletion of the Ck gene segment, or to any of the Vk gene segments, resulting in deletion of the entire Jk-Ck region. Both types of Kde rearrangements result in deletion of the two IGK gene enhancers (iEk and 3'Ek), most likely precluding further rearrangements in the IGK locus.
Figure 6:
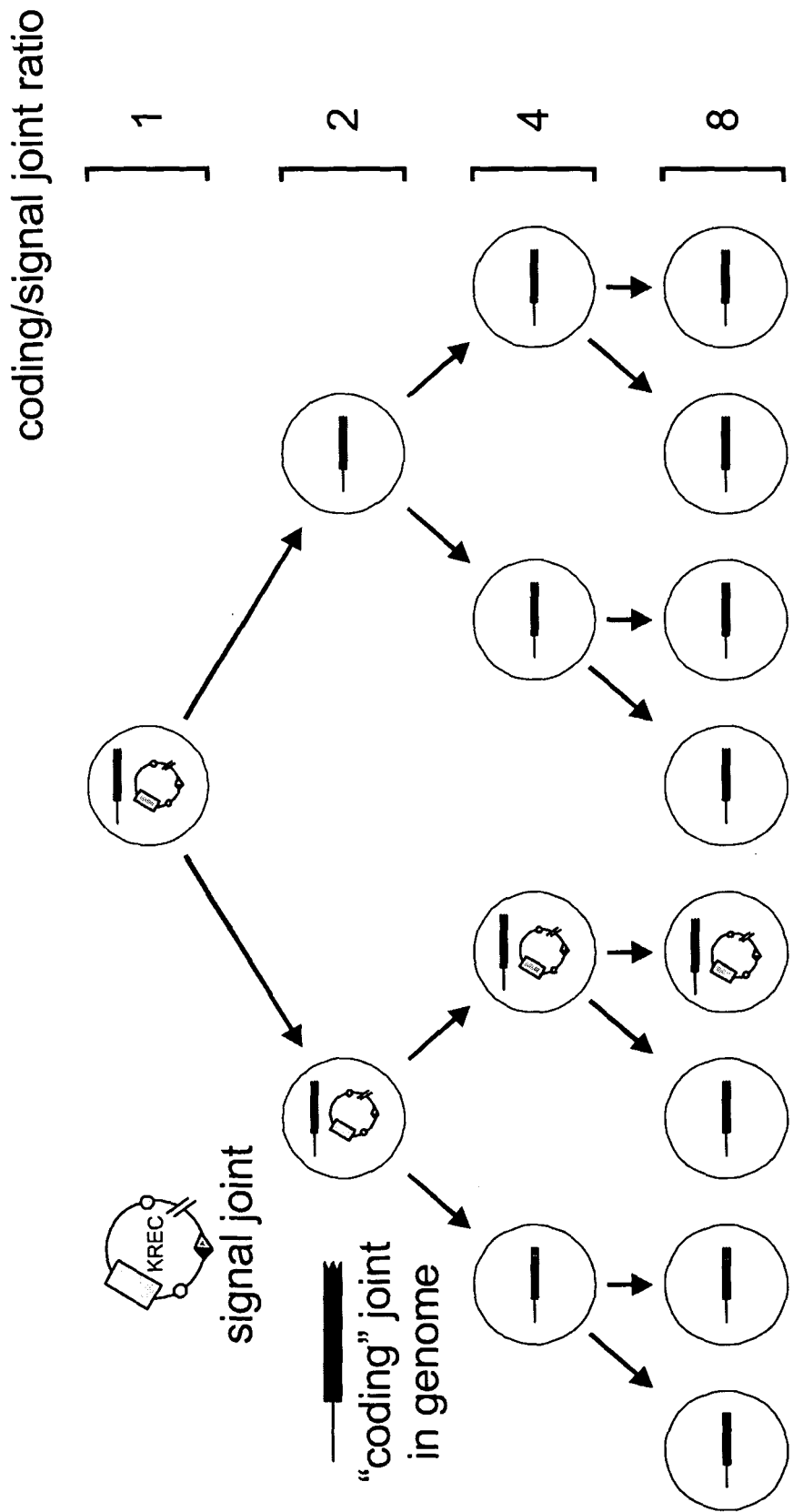
FIG. 6: Presumed signal/coding joint ratios during consecutive divisions of B cells. With each round of replication, the chromosomal-coding joint nucleotide sequence in a B cell is replicated, whereas the episomal circular excision product carrying the signal joint nucleotide sequence remains intact yet is not replicated. Consequently, with each round of replication of a B cell, the episomal products are diluted during division such that the signal/coding joint ratio is progressively reduced.
Figure 7:
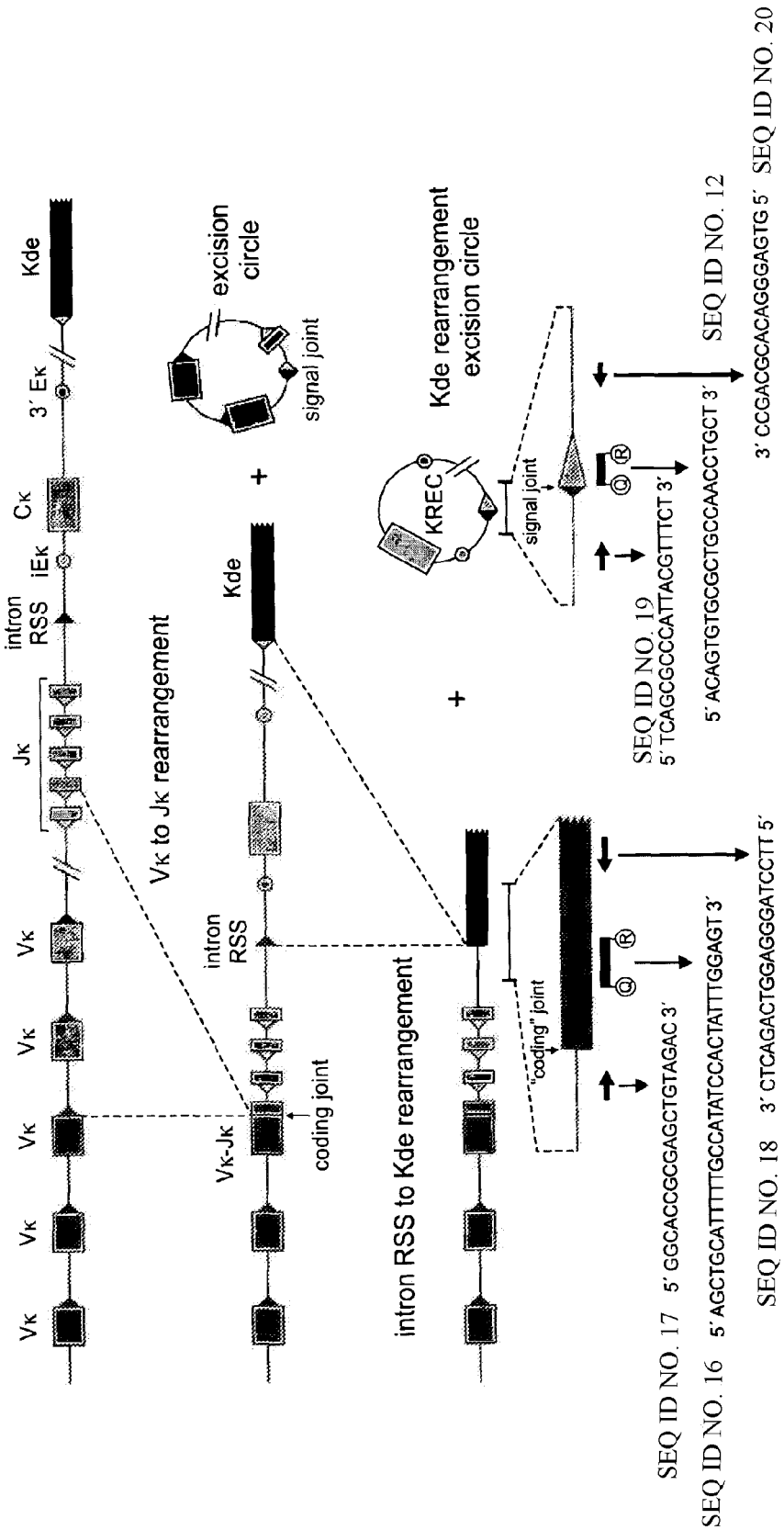
FIG. 7: Real-time quantitative PCR-based detection of signal and coding joints of intronRSS-Kde rearrangements. The relative positioning of primers and TaqMan probes is indicated.
Figure 8:
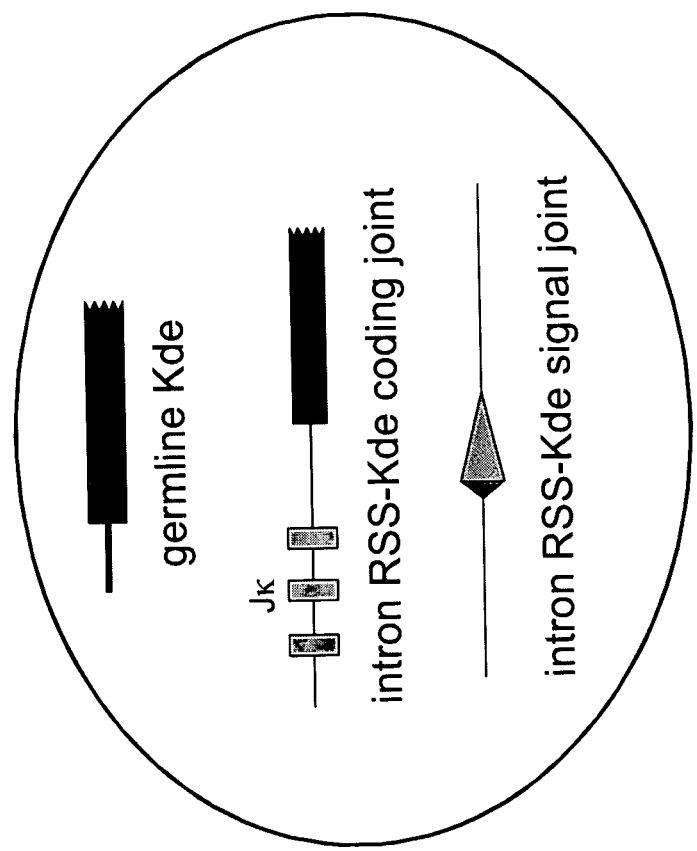
FIG. 8: Schematic representation of the control cell line. The control cell line is stably transformed with the sequence of an extrachromosomal KREC containing a signal joint sequence of an intronRSS-Kde rearrangement. It also contains the coding joint sequence resulting from an intronRSS to Kde rearrangement as well as a germline Kde segment on the second IGK allele. In contrast to the expanding B cells, the coding joint and the signal joint sequences that are present in the control cell line are both replicated during cell division. Consequently, the ratio between the two can be set at 1.0.
Figure 9A:
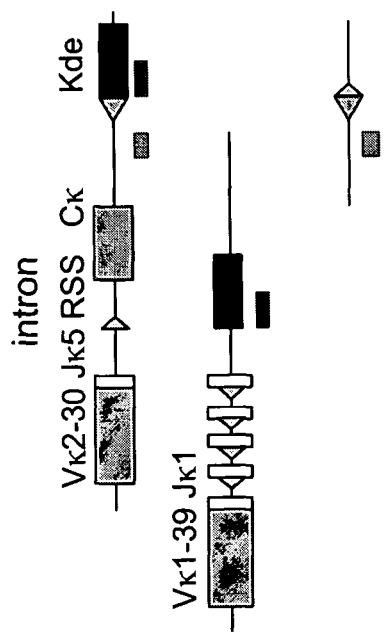
FIG. 9: Generation of the KREC control B-cell line with one intron-RSS-Kde-coding joint and one signal joint per genome. Panel A: Schematic representation of the IGK loci of the U698-M cell line and the intron-RSS-Kde signal joint construct. Panel B: Southern blot of the original U698-M cell line and three single clones that contain a unique insertion of the signal joint construct.
Figure 9B:
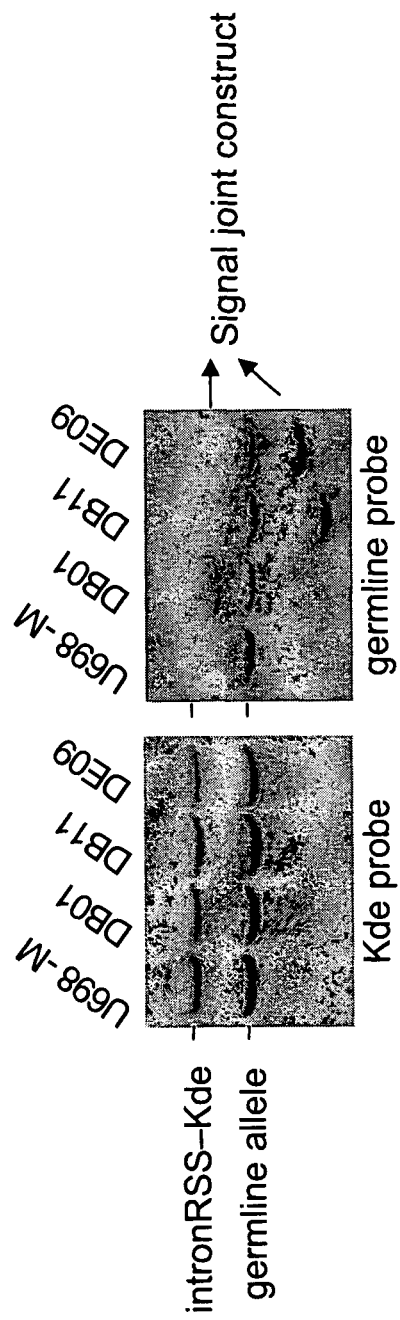

Materials and Methods
Generation and Transduction of the intron-RSS-Kde Signal Joint construct into the U698-M B-cell Line The KREC signal joint construct was cloned into the retroviral LZRS-IRES-eGFP vector after introducing an EcoRI restriction site 60 bp upstream of the Kde RSS heptamer sequence (FIG. 9, Panel A). The retroviral LZRS- KREC construct and an empty vector control were transfected into Phoenix amphotropic packaging cell lines using Fugene-6 (Roche Molecular Biochemicals, Branchbury, N.Y.). Stable high-titer producer clones were selected with puromycin (1 µg/ml). The U698-M pre-B-cell line was cultured for several days in RPMI 1640 medium containing 10% FCS and antibiotics before transduction using Retronectin-coated petri dishes (Takara, Shiga, Japan) and recombinant retrovirus containing supernatant for two days, with daily replenishing of retroviral supernatant. GFP-positive cells were single-cell sorted using a FACSDiVa cell sorter (BD Biosciences, Santa Clara, Calif.). Individual clones were selected for dim GFP expression suggesting a single genomic integration.

Southern Blot Analysis of Individual U698-M KREC Cell Line Clones

DNA isolation and Southern blot analysis was performed as previously described.[5] In short, 15 to 20 µg genomic DNA was digested with EcoRI, separated in a 0.7% agarose gel, and vacuum blotted. The configuration of the IGK locus was determined using $^{32}$P-labeled probes specific for the Kde regions, [22] and for the regions upstream of Kde, which are deleted from the genome after an intronRSS-Kde rearrangement and are present on the KREC construct (FIG. 9, Panel B).

Purification of (Precursor) B-cell Populations from BM, PB and Tonsil

Precursor B cells were obtained from freshly isolated BM samples of three healthy children (ages 3 to 16) as described.[34] The BM samples were taken for quality control of the graft. When a small amount of BM (0.5 to 2.0 ml) was left over after the required tests, it was used for these studies.

Four CD19-positive B-cell subsets were purified from PB of five healthy adults by sorting on a FACSDiVa cell sorter after staining of post-Ficoll mononuclear cells, that were MACS sorted using CD19 beads (Miltenyi Biotec), with CD27-FITC (LT27; Serotec, Raleigh, N.C.), IgD-PE (Southern Biotechnology Associates, Inc., Birmingham, Ala.), CD19-PE-Cy7 (SJ25C1), CD5-APC (L17F12; both from BD Biosciences).

Six tonsillar B-cell subsets were purified from tonsils of three children on a FACSDiVa after direct staining on freeze-thawed material. Additional monoclonals used were CD77-FITC (5B5) and CD38-APC (HB7; both from BD Biosciences).

All fractions were obtained with a purity of >95%. See FIG. 10 for precise immunophenotype of each B-cell subset and for their relative frequency.

Real-time Quantitative PCR and Calculation of the Proliferative History of B-cell Populations Primers and probes were designed to specifically amplify the intronRSS-Kde rearrangement and the intronRSS-Kde KREC using TaqMan-based real-time quantitative (RQ-) PCR from DNA isolated from cell lines and primary material. The RQ-PCR mixture of 25 µl contained TaqMan Universal MasterMix (Applied Biosystems, Foster City, Calif.), 900 nM of each primer, 100 nM of each FAM-TAMRA labeled probe, 50 ng of DNA, 0.4 ng BSA, and was run on the ABIPRISM 7700 sequence detection system (Applied Biosystems).[33, 35] The primer-probe sets for both rearrangements were tested for comparable efficiency using DNA isolated from the U698-M clone DB01 that contains one intronRSS-Kde rearrangement and one KREC construct per genome.

In all experiments, the cycle threshold ($C_T$) was set at 0.03 and the $C_T$ values of the intronRSS-Kde rearrangement and the KREC were compared for each sample. Since both PCR amplification and cell division are exponential multiplication processes with base 2, the $\Delta C_T$ ($C_{T\ (intronRSS-Kde)} - C_{T\ (KREC)}$) from a given fraction, represents the average number of cell divisions these cells have undergone.

Results

Generation of a Stable B-cell Line with intronRSS-Kde Signal Joint Construct

Southern blotting with a Kde probe and sequencing of PCR-amplified IGK gene rearrangements revealed that the IgK$^+$ B-cell line U698-M had two Vκ-Jκ rearrangements, one of which was out-of-frame and contained an intronRSS-Kde rearrangement (FIG. 9, Panels A and B). Using retroviral transduction, an intronRSS-Kde construct was inserted in the genome of the U698-M cell line. Individual clones were sorted and for three clones, Southern blotting analysis revealed a single insertion per genome (FIG. 9, Panel B).

Isolation of (Precursor) B-cell Populations from Human BM, Tonsil and PB

Figure 10A:
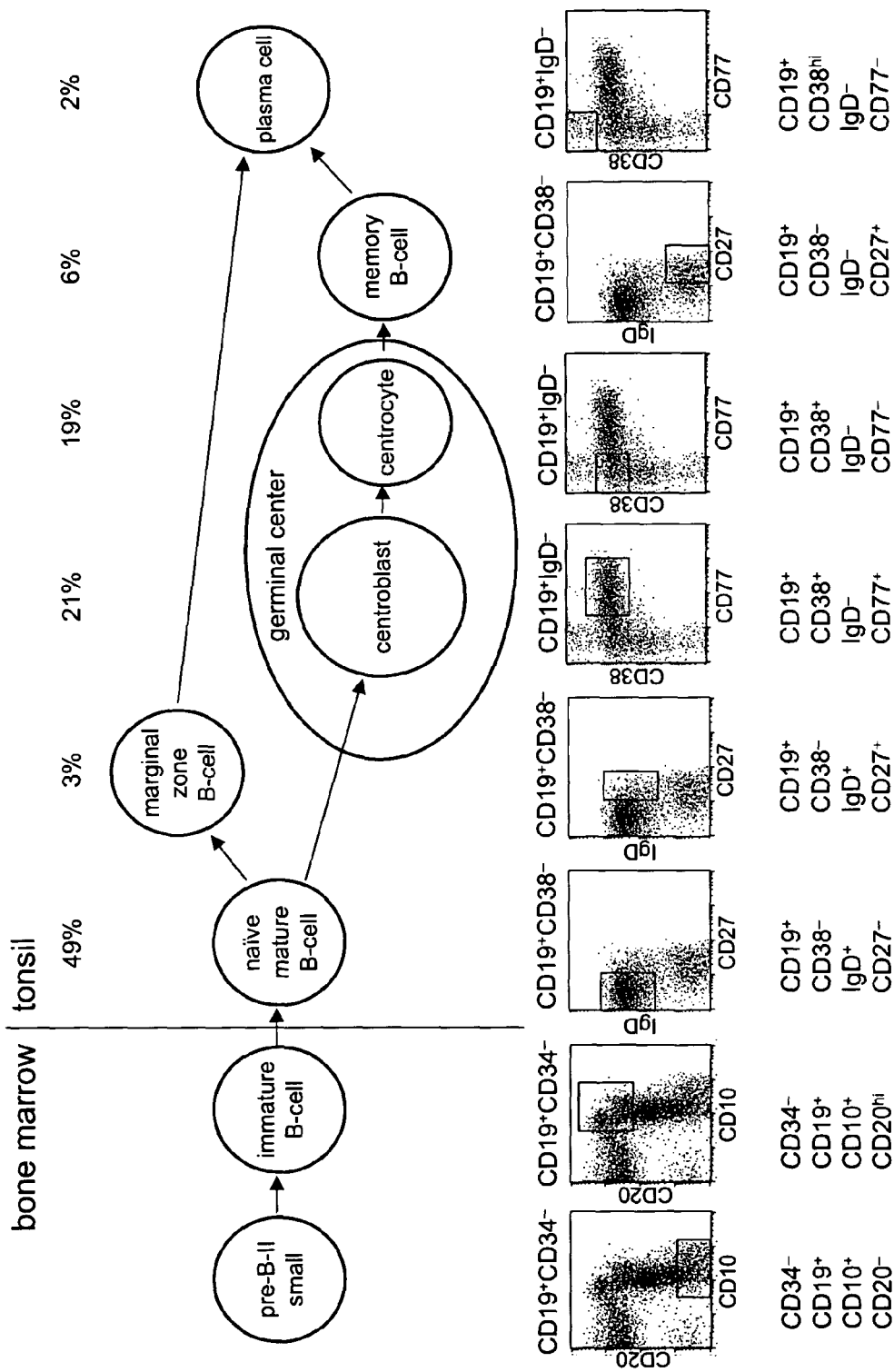
FIG. 10: The replicative history of B-cell subsets from bone marrow, tonsil and peripheral blood. A. The B-cell subsets isolated from bone marrow and tonsil represent several consecutive and parallel differentiation stages. B. Four B-cell subsets were isolated from peripheral blood. C. Number of cell divisions reflecting the replicative history of B-cell subsets from bone marrow, tonsil and peripheral blood.
Figure 10B:
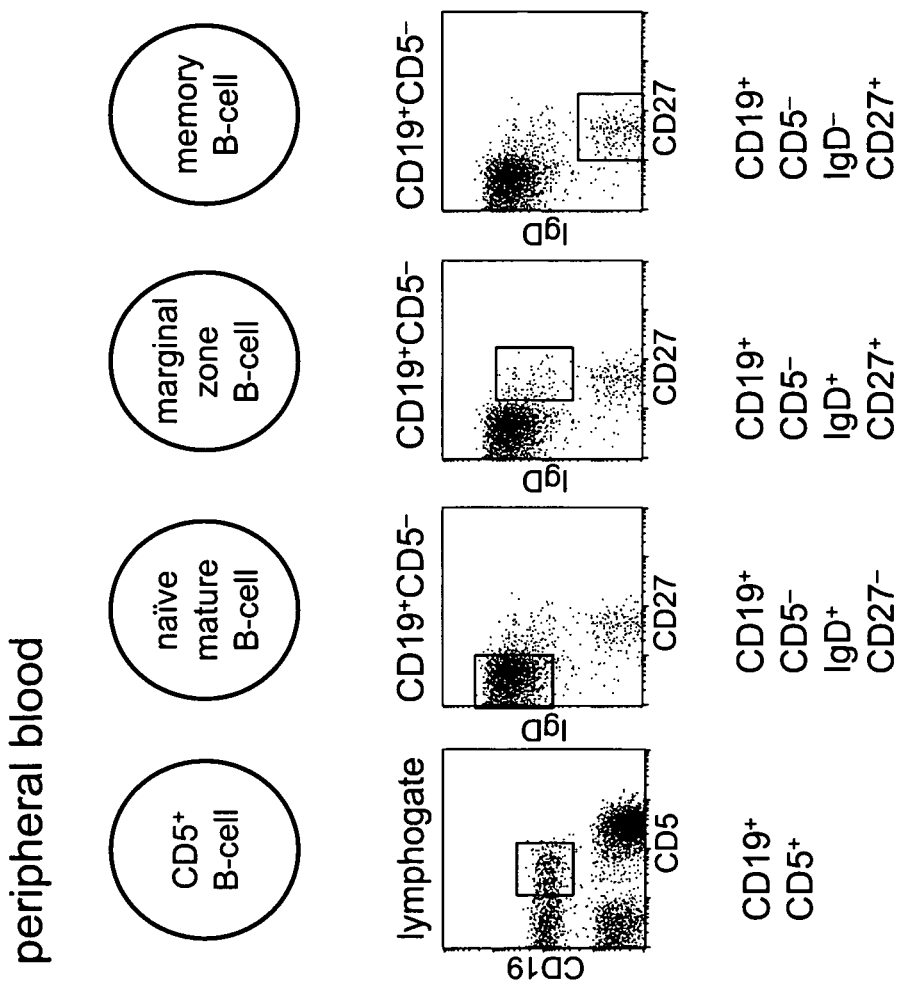

All precursor B-cell subsets from bone marrow and mature B-cell subsets from PB and tonsil were isolated using previously established markers.[34, 36, 37, 38] Small pre-B-II cells (CD19$^+$CD34$^-$CD10$^+$CD20$^-$), and immature B cells (CD19$^+$CD34$^-$CD10$^+$CD20$^{hi}$) were isolated from BM (FIG. 10A). From human tonsil, the following six B-cell subsets were isolated: naïve B cells (CD19$^+$CD38$^-$IgD$^{30}$ CD27$^-$), marginal zone B cells (CD19$^+$CD38$^-$IgD$^+$CD27$^+$), centroblasts (CD19$^+$CD38$^+$IgD$^-$CD77$^+$), centrocytes (CD19$^+$CD38$^+$IgD$^-$CD77$^-$) memory B cells (CD19$^+$CD38$^-$IgD$^-$CD27$^+$), and plasma cells (CD19$^+$CD38$^{hi}$). From PB,the recirculating counterparts of tonsil B-cell subsets were isolated: naïve B cells (CD19$^+$CD5$^-$IgD$^+$CD27$^-$), marginal zone B cells (CD19$^+$CD5$^-$IgD$^+$CD27$^+$), memory B cells (CD19$^+$CD5$^-$IgD$^-$CD27$^+$). In addition, the CD5$^+$ B-cell subset was isolated (CD19$^+$CD5$^+$IgD$^+$CD27$^-$) from PB (FIG. 10B).

The Extent of Antigen-induced B-cell Proliferation in Secondary Lymphoid Organs

Figure 10C:
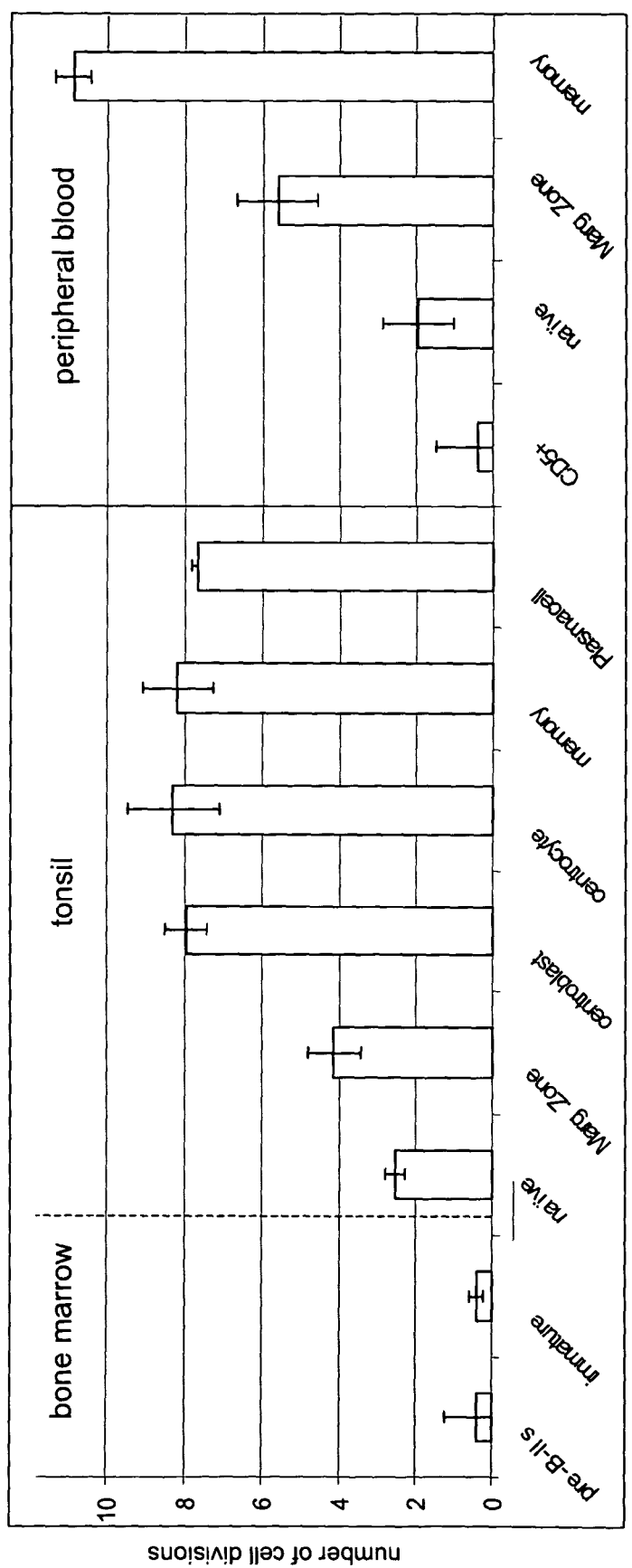

In precursor B-cell differentiation, the majority of the intronRSS-Kde rearrangements is initiated in small pre-B-II cells and remains high in immature and mature B cells.[34] We quantified the amount of intronRSS-Kde rearrangements and the intronRSS-Kde KREC in small pre-B-II and immature B cells from BM using TaqMan RQ-PCR. The $\Delta C_T$ ($C_{T\ (intronRSS-Kde)} - C_{T\ (KREC)}$), which represents the average amount of cell divisions of the B cells, was 0.4 (FIG. 10C). This indicates that precursor B cells in human BM do not proliferate after the intronRSS to Kde rearrangement.

In contrast to precursor B cells in BM, mature B cells in tonsils from children do show a clear replicative history (FIG. 10C). Naïve mature B cells show on average a replicative history of 2.5 cell divisions. Marginal zone B cells underwent on average 4.1 cell divisions, which is clearly more than what is found in naïve B cells. Finally, the centroblasts and centrocytes in the germinal center, the memory B cells and the plasma cells in childhood tonsil showed a replicative history of about eight cell divisions. As expected by the nature of them, the centroblasts formed the major proliferative subset. It can thus be concluded that naïve B cells have already proliferated before entering the germinal center in which they subsequently give rise to on average $2^{(8-2.5)}$=45 daughter cells.

Many mature B-cell subsets circulate in PB and can be identified as their counterparts found in secondary lymphoid organs. Naïve mature B cells in adult PB were found to have a replicative history of 1.9, which is almost similar to naive mature B cells in tonsil (FIG. 10C). Furthermore, circulating marginal zone B cells and memory B cells in adult PB were found to have a replicative history of 5.6 and 10.9 cell divisions, respectively. For both populations, the number of cell cycles is higher in adult PB as compared to childhood tonsil. The fourth major population isolated from PB was the CD5+ B-cell subset. This subset had a replicative history of only 0.4, which is similar to what was found for small pre-B-II and immature B cells in BM. In contrast to CD5− naïve mature B cells, the CD5+ B-cell subset does not show a proliferative history in the peripheral B-cell compartment.

5. Van Dongen J. J. M., and I. L. M. Wolvers-Tettero. Analysis of immunoglobulin and T cell receptor genes. Part I: Basic and technical aspects. *Clin. Chim. Acta.* 1991; 198:1-91.
6. Davis M. M., and P. J. Björkman. T-cell antigen receptor genes and T-cell recognition. *Nature* 1988; 334:395-402.
7. Lieber M. R. The mechanism of V(D)J recombination: a balance of diversity, specificity, and stability. *Cell* 1992; 70:873-876.

TABLE 1

Primers and probes for RQ-PCR detection of corresponding coding and signal joints of Kde rearrangements and germline Kde alleles

| | Oligonucleotides for RQ-PCR | | | | Application | | |
|---|---|---|---|---|---|---|---|
| Type | Code | 5' sequence 3' | SEQ ID NO | 5' Position from junction | Vk-Kde | intron RSS-Kde | germline Kde |
| Kde-coding joint and Kde germline detection | | | | | | | |
| Primer | Vk3-20 Up | TCTCACCATCAGCAGACTGGAG | 1 | −71 | + | − | − |
| Primer | Intron Up1 | CCGATTAATGCTGCCGTAGC | 2 | −34 | − | + | − |
| Primer | Intron Up2 | CCCGATTAATGCTGCCGTAG | 3 | −35 | − | + | − |
| Primer | Intron Up3 | GGCACCGCGAGCTGTAGAC | 17 | −152 | − | + | − |
| Primer | Kde Down1 | TTCCTAGGGAGGTCAGACTC | 14 | +91 | + | + | + |
| Primer | Kde Down2 | CCTAGGGAGCAGGGAGGCTT | 5 | +109 | + | + | + |
| Primer | Kde Down3 | CCTCAGAGGTCAGAGCAGGTTGTCCTA | 6 | +132 | + | + | + |
| Primer | Kde Down4 | TACAGACAGGTCCTCAGAGGTCAG | 7 | +143 | + | + | + |
| Primer | Kde Down5 | CCCTTCATAGACCCTTCAGGCAC | 15 | +185 | + | + | + |
| Probe | T-Kde | AGCTGCATTTTTGCCATATCCACTATTTGGAGT | 16 | +43 | + | + | + |
| Kde signal joint (KREC) and Kde germline detection | | | | | | | |
| Primer | Vk3-20 Down | CTATCTGTAAAGGAAGCAGCTGGTA | 8 | +84 | + | − | − |
| Primer | Kde-germline Up | CTTACCCTAGAGTTTCTGCACGG | 9 | −43 | + | + | + |
| Primer | Int-Kde BREC F | TCAGCGCCCATTACGTTTCT | 19 | +58 | − | + | − |
| Primer | Int-Kde BREC R | GTGAGGGACACGCAGCC | 20 | −90 | + | + | + |
| Probe | Kde-RSS | ACAGTGTGCGCTGCCAACCTGCT | 12 | −24 | + | + | + |
| Probe | T-Kde-RSS_2 | CCAGCTCTTACCCTAGAGTTTCTGCACGG | 13 | −55 | + | + | + |

REFERENCES (THE CONTENTS OF EACH OF WHICH ARE INCORPORATED HEREIN BY THIS REFERENCE).

1. Alt F. W., T. K. Blackwell, and G. D. Yancopoulos. Development of the primary antibody repertoire. *Science* 1987; 238:1079-1087.
2. Schroeder H. W., Jr., J. L. Hillson, and R. M. Perlmutter. Early restriction of the human antibody repertoire. *Science* 1987; 238:791-793.
3. Ghia P., E. ten Boekel, A. G. Rolink, and F. Melchers. B-cell development: a comparison between mouse and man. *Immunol. Today* 1998; 19:480-485.
4. Tonegawa S. Somatic generation of antibody diversity. *Nature* 1983; 302:575-581.
8. Schatz D. G., M. A. Oettinger, and D. Baltimore. The V(D)J recombination activating gene, RAG-1. *Cell* 1989; 59:1035-1048.
9. Oettinger M. A., D. G. Schatz, C. Gorka, and D. Baltimore. RAG-1 and RAG-2, adjacent genes that synergistically activate V(D)J recombination. *Science* 1990; 248: 1517-1523.
10. Desiderio S. V., G. D. Yancopoulos, M. Paskind, E. Thomas, M. A. Boss, N. Landau, F. W. Alt, and D. Baltimore. Insertion of N regions into heavy-chain genes is correlated with expression of terminal deoxytransferase in B cells. *Nature* 1984; 311:752-755.
11. Korsmeyer S. J., P. A. Hieter, S. O. Sharrow, C. K. Goldman, P. Leder, and T. A. Waldmann. Normal human B cells display ordered light chain gene rearrangements and deletions. *J. Exp. Med.* 1982; 156:975-985.
12. Van Der Burg M., B. H. Barendregt, T. Szczepanski, E. R. Van Wering, A. W. Langerak, and J. J. M. Van Dongen. Immunoglobulin light chain gene rearrangements display hierarchy in absence of selection for functionality in precursor-B-ALL. *Leukemia* 2002; 16:1448-1453.
13. Korsmeyer S. J., P. A. Hieter, J. V. Ravetch, D. G. Poplack, T. A. Waldmann, P. Leder. Developmental hierarchy of immunoglobulin gene rearrangements in human leukemic pre-B-cells. *Proc. Natl. Acad. Sci. U.S.A.* 1981; 78:7096-7100.
14. van der Burg M., T. Tumkaya, M. Boerma, S. de Bruin-Versteeg, A. W. Langerak, and J. J. M. van Dongen. Ordered recombination of immunoglobulin light chain genes occurs at the IGK locus but seems less strict at the IGL locus. *Blood* 2001; 97:1001-1008.
15. Hieter P. A., S. J. Korsmeyer, T. A. Waldmann, and P. Leder. Human immunoglobulin kappa light-chain genes are deleted or rearranged in lambda-producing B cells. *Nature* 1981; 290:368-372.
16. Siminovitch K. A., A. Bakhshi, P. Goldman, and S. J. Korsmeyer. A uniform deleting element mediates the loss of kappa genes in human B cells. *Nature* 1985; 316:260-262.
17. Klobeck H. G., and H. G. Zachau. The human CK gene segment and the kappa-deleting element are closely linked. *Nucleic Acids Res.* 1986; 14:4591-4603.
18. Graninger W. B., P. L. Goldman, C. C. Morton, S. J. O'Brien, and S. J. Korsmeyer. The kappa-deleting element. Germline and rearranged, duplicated and dispersed forms. *J. Exp. Med.* 1988; 167:488-501.
19. Langerak A. W., B. Nadel, A. De Torbal, I. L. M. Wolvers-Tettero, E. J. Van Gastel-Mol, B. Verhaaf, U. Jager, and J. J. M. Van Dongen. Unraveling the Consecutive Recombination Events in the Human IGK Locus. *J. Immunol.* 2004; 173:3878-3888.
20. Inlay M., F. W. Alt, D. Baltimore, and Y. Xu. Essential roles of the kappa light chain intronic enhancer and 3' enhancer in kappa rearrangement and demethylation. *Nat. Immunol.* 2002; 3:463-468.
21. Feddersen R. M., D. J. Martin, and B. G. Van Ness. The frequency of multiple recombination events occurring at the human Ig kappa L chain locus. *J. Immunol.* 1990; 144:1088-1093.
22. Beishuizen A., M. A. Verhoeven, E. J. Mol, and J. J. M. van Dongen. Detection of immunoglobulin kappa light-chain gene rearrangement patterns by Southern blot analysis. *Leukemia* 1994; 8:2228-2236.
23. Beishuizen A., M. A. C. de Bruijn, M. J. Pongers-Willemse, M.-A. J. Verhoeven, E. R. van Wering, K. Hählen, T. M. Breit, S. de Bruin-Versteeg, H. Hooijkaas, and J. J. M. van Dongen. Heterogeneity in junctional regions of immunoglobulin kappa-deleting element rearrangements in B cell leukemias: a new molecular target for detection of minimal residual disease. *Leukemia* 1997; 11:2200-2207.
24. Van Lochem E. G., Y. M. Wiegers, R. van den Beemd, K. Hahlen, J. J. M. van Dongen, and H. Hooijkaas. Regeneration pattern of precursor B cells in bone marrow of acute lymphoblastic leukemia patients depends on the type of preceding chemotherapy. *Leukemia* 2000; 14:688-695.
25. Van Wering E. R., B. E. van der Linden-Schrever, T. Szczepanski, M. J. Willemse, E. A. Baars, H. M. van Wijngaarde-Schmitz, W. A. Kamps, and J. J. M. van Dongen. Regenerating normal B-cell precursors during and after treatment of acute lymphoblastic leukaemia: implications for monitoring of minimal residual disease. *Br. J. Haematol.* 2000; 110:139-146.
26. Leitenberg D., J. M. Rappeport, B. R. Smith. B-cell precursor bone marrow reconstitution after bone marrow transplantation. *Am. J. Clin. Pathol.* 1994; 102:231-6.
27. Linton P. J., and K. Dorshkind. Age-related changes in lymphocyte development and function. *Nat. Immunol.* 2004; 5:133-139.
28. Hazenberg M. D., S. A. Otto, J. W. Cohen Stuart, M. C. M. Verschuren, J. C. Borleffs, C. A. Boucher, R. A. Coutinho, J. M. Lange, T. F. Rinke de Wit, A. Tsegaye, J. J. M. Van Dongen, D. Hamann, R. J. de Boer, and F. Miedema. Increased cell division but not thymic dysfunction rapidly affects the T-cell receptor excision circle content of the naïve T cell population in HIV-1 infection. *Nat. Med.* 2000; 6:1036-1042.
29. Hazenberg M. D., M. C. Verschuren, D. Hamann, F. Miedema, and J. J. M. van Dongen. T cell receptor excision circles as markers for recent thymic emigrants: basic aspects, technical approach, and guidelines for interpretation. *J. Mol. Med.* 2001; 79:631-40.
30. Verschuren M. C., I. L. Wolvers-Tettero, T. M. Breit, J. Noordzij, E. R. van Wering, and J. J. M. van Dongen. Preferential rearrangements of the T cell receptor-delta-deleting elements in human T cells. *J. Immunol.* 1997; 158:1208-16.
31. Pongers-Willemse M. J., O. J. H. M. Verhagen, G. J. M. Tibbe, J. M. Wijkhuijs, V. De Haas, E. Roovers, C. E. Van der Schoot, and J. J. M. Van Dongen. Real-time quantitative PCR for the detection of minimal residual disease in acute lymphoblastic leukemia using junctional regions specific TaqMan probes. *Leukemia* 1998; 12:2006-2014.
32. Van der Velden V. H. J., M. J. Willemse, C. E. van der Schoot, E. R. van Wering, J. J. M. van Dongen. Immunoglobulin kappa-deleting element rearrangements in precursor-B acute lymphoblastic leukemia are stable targets for detection of minimal residual disease by real-time quantitative PCR. *Leukemia* 2002; 16:928-936.
33. Van der Velden V. H. J., A. Hochhaus, G. Cazzaniga, T. Szczepanski, J. Gabert, and J. J. M. Van Dongen. Detection of minimal residual disease in hematologic malignancies by real-time quantitative PCR: principles, approaches, and laboratory aspects. *Leukemia* 2003; 17:1013-1034.
34. Van Zelm et al. Ig gene rearrangement staps are initiated in early human precursor B-cell subsets and correlate with specific transcription factor expression. *J. Immunol.* 2005, in press.
35. Moppett J., V. H. J. Van der Velden, A. J. Wijkhuijs, J. Hancock, J. J. M. Van Dongen, and N. Goulden. Inhibition affecting RQ-PCR-based assessment of minimal residual disease in acute lymphoblastic leukemia: reversal by addition of bovine serum albumin. *Leukemia* 2003;17: 268-270.
36. Weller S., M. C. Braun, B. K. Tan, A. Rosenwald, C. Cordier, M. E. Conley, A. Plebani, D. S. Kumararatne, D. Bonnet, O. Tournilhac, G. Tchernia, B. Steiniger, L. M. Staudt, J. L. Casanova, C. A. Reynaud, and J. C. Weill. Human blood IgM "memory" B cells are circulating splenic marginal zone B cells harboring a prediversified immunoglobulin repertoire. *Blood* 2004; 104:3647-3654.
37. Pascual V., Y. J. Liu, A. Magalski, O. De Bouteiller, J. Bancherau, and J. D. Capra. Analysis of somatic mutation in five B cell subsets of human tonsil. *J. Exp. Med.* 1994; 180:329-339.
38. Klein U., Y. Tu, G. A. Stolovitzky, J. L. Keller, J. Haddad, V. Miljkovic, G. Cattoretti, A. Califano, and R. Dalla-Favera. Transcriptional analysis of the B cell germinal center reaction. *Proc. Natl. Acad. Sci.* U.S.A. 2003; 100:2639-2644.

What is claimed is:

1. A method of determining the replicative history of a lymphocyte population, comprising:
   a) obtaining at least one population of lymphocytes;
   b) assaying the quantity of an extrachromosomally maintained signal joint arising from formation of a chromosomal coding joint in the lymphocyte population;
   c) assaying the quantity of the chromosomal coding joint in the lymphocyte population
   d) providing a population of control cells, which cells have been transformed with at least one exogenously introduced nucleic acid encoding a nucleotide sequence of a signal joint and/or at least one exogenously introduced nucleic acid encoding a nucleotide sequence of a coding joint such that said control cells have both a nucleic acid encoding a nucleotide sequence of a signal joint and a nucleic acid encoding a nucleotide sequence of a coding joint, and assaying the quantity of said signal joint nucleotide sequence and said coding joint nucleotide sequence wherein the quantity of said signal joint nucleotide sequence and said coding joint nucleotide sequence provides a control result; and
   e) determining the replicative history of the lymphocyte population based on a ratio of the quantity of the chromosomal coding joint to the quantity of the extrachromosomally maintained signal joint in the lymphocyte population, wherein the control result is used as a control for the ratio between the chromosomal coding joint and extrachromosomally maintained signal joint.

2. The method of claim 1, wherein the lymphocyte population is a B cell population.

3. The method of claim 2, wherein the B cell population is selected from a group consisting of: a precursor B cell population, a neonatal cord blood B cell population, a childhood peripheral blood B cell population, an adult peripheral blood B cell population, a B cell population obtained from a tonsil, a B cell population obtained from a lymph node, a B cell population obtained from bone marrow, a B cell population obtained from a germinal center, a B cell population obtained from peripheral blood, a virgin B cell population, a memory B cell population, a B cell population with an IgH class switch, and a B cell population without an IgH class switch.

4. The method of claim 2, wherein assaying comprises RQ-PCR analysis.

5. The method of claim 1, wherein the lymphocytes are obtained from a subject who has received a bone marrow transplant.

6. The method of claim 1, wherein the chromosomal coding joint and the extrachromosomally maintained signal joint are formed from an end-stage gene rearrangement.

7. The method of claim 6, wherein the end-stage gene rearrangement is an intron RSS to Kde rearrangement or a VK to Kde rearrangement.

8. The method of claim 6, wherein the end-stage gene rearrangement is an intron RSS to Kde rearrangement rearrangement.

9. The method of claim 8, wherein assaying comprises RQ-PCR analysis.

10. The method of claim 1, wherein the chromosomal coding joint and the extrachromosomally maintained signal joint are formed from a VH to DH rearrangement.

11. The method of claim 1, wherein assaying comprises real-time quantitative (RQ) PCR analysis.

12. The method of claim 11, wherein the RQ-PCR analysis utilizes at least one nucleic acid amplification primer selected from the group consisting of SEQ ID NOs: 1-3, 5-9, 17, 19, and 20.

13. The method of claim 1, wherein at least one exogenously introduced nucleic acid encoding the signal joint nucleotide sequence and at least one exogenously introduced nucleic acid encoding the coding joint nucleotide sequence are stably integrated in the genome of the control cell.

14. The method of claim 1, wherein the signal joint nucleotide sequence and the coding joint nucleotide sequence of the control cells are homologous to a signal joint nucleotide sequence and a coding joint nucleotide sequence formed as the result of an intron-RSS-Kde rearrangement.

15. The method of claim 1, wherein said control cells further comprise a nucleic acid comprising a Kde nucleic acid sequence in germline configuration.

* * * * *